(12) United States Patent
Wincheski et al.

(10) Patent No.: US 6,888,346 B2
(45) Date of Patent: May 3, 2005

(54) MAGNETORESISTIVE FLUX FOCUSING EDDY CURRENT FLAW DETECTION

(75) Inventors: Russell A. Wincheski, Williamsburg, VA (US); Min Namkung, Yorktown, VA (US); John W. Simpson, Tabb, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/021,683

(22) Filed: Nov. 28, 2001

(65) Prior Publication Data

US 2002/0130659 A1 Sep. 19, 2002

Related U.S. Application Data

(60) Provisional application No. 60/253,352, filed on Nov. 28, 2000.

(51) Int. Cl.[7] .............................................. G01N 27/82
(52) U.S. Cl. ....................................... 324/235; 324/240
(58) Field of Search ................................ 324/229–240, 324/252; 702/38

(56) References Cited

U.S. PATENT DOCUMENTS

| 4,134,067 A | 1/1979 | Woodbury |
| 4,228,687 A | 10/1980 | Fraser |
| 4,292,848 A | 10/1981 | Rainey et al. |

(Continued)

OTHER PUBLICATIONS

Buzz Wincheski and Min Namkung, "Electromagnetic Detection of Fatigue Cracks Under Protruding Head Ferromagnetic Fasteners," Third Joint FAA/DoD/NASA Conference of Aging Aircraft, 1st ed., FAA/DoD/NASA (Albuquerque, NM), p. 1–9, (Sep. 20, 1999).

(Continued)

*Primary Examiner*—N. Le
*Assistant Examiner*—Reena Aurora
(74) *Attorney, Agent, or Firm*—Robin W. Edwards

(57) ABSTRACT

A giant magnetoresistive flux focusing eddy current device effectively detects deep flaws in thick multilayer conductive materials. The probe uses an excitation coil to induce eddy currents in conducting material perpendicularly oriented to the coil's longitudinal axis. A giant magnetoresistive (GMR) sensor, surrounded by the excitation coil, is used to detect generated fields. Between the excitation coil and GMR sensor is a highly permeable flux focusing lens which magnetically separates the GMR sensor and excitation coil and produces high flux density at the outer edge of the GMR sensor. The use of feedback inside the flux focusing lens enables complete cancellation of the leakage fields at the GMR sensor location and biasing of the GMR sensor to a location of high magnetic field sensitivity. In an alternate embodiment, a permanent magnet is positioned adjacent to the GMR sensor to accomplish the biasing. Experimental results have demonstrated identification of flaws up to 1 cm deep in aluminum alloy structures. To detect deep flaws about circular fasteners or inhomogeneities in thick multi-layer conductive materials, the device is mounted in a hand-held rotating probe assembly that is connected to a computer for system control, data acquisition, processing and storage.

32 Claims, 18 Drawing Sheets

U.S. PATENT DOCUMENTS

| | | | | |
|---|---|---|---|---|
| 4,303,885 A | * | 12/1981 | Davis et al. | 324/237 |
| 4,792,755 A | * | 12/1988 | Huschelrath et al. | 324/225 |
| 5,399,968 A | | 3/1995 | Sheppard et al. | |
| 5,475,304 A | | 12/1995 | Prinz | |
| 5,510,709 A | | 4/1996 | Hurley et al. | |
| 5,554,933 A | | 9/1996 | Logue | |
| 5,565,236 A | | 10/1996 | Gambino et al. | |
| 5,617,024 A | | 4/1997 | Simpson et al. | |
| 5,648,721 A | | 7/1997 | Wincheski et al. | |
| 5,698,977 A | * | 12/1997 | Simpson et al. | 324/209 |
| 5,847,562 A | * | 12/1998 | Fulton et al. | 324/229 |
| 6,150,809 A | | 11/2000 | Tiernan et al. | |
| 6,504,363 B1 | * | 1/2003 | Dogaru et al. | 324/235 |

OTHER PUBLICATIONS

Buzz Wincheski and Min Namkung, "Deep Flaw Detection with Giant Magnetoresistive (GMR) Based Self–Nulling Probe," 26th Annual Review of Progress in QNDE, 1st ed., QNDE (Montreal, Canada), p. 1–8, (Jul. 25, 1999).

Buzz Wincheski and Min Namkung, "Development of Very Low Frequency Self–Nulling Probe for Inspection of Thick–Layered Aluminum Structures," 1998 Review of Progress in Quantitative NDE, 1st ed., p. 1–8, (Aug. 1, 1998).

Buzz Wincheski, Min Namkung, and John W. Simpson, "Magnetoresistive Sensor Based Rotating Probe System for Detection of Deep Fatigue Cracks Under Airplane Fasteners," The Fourth Joint NASA/FAA/DoD Conference on Aging Aircraft, 2000, 1st ed., NASA/FAA/DoD (USA), p. 1–10, (Nov. 28, 2000).

Buzz Wincheski, Jim Fulton, Ron Todhunter, & John Simpson, "Development and Testing of Rotating Probe Method for Airframe Rivet Inspection," Review of Progress in Quantitative Nondestructive Evaluation, Plenum Press (New York), p. 2133–2140.

* cited by examiner

Amplitude (mV)
6.5  7.0  7.5  8.0  8.5

Amplitude (mV)
6.5  7.0  7.5

Amplitude (mV)
7.4  7.6  7.8  8.0

Amplitude (mV)
7.4  7.6  7.8  8.0

MAGNETORESISTIVE FLUX FOCUSING EDDY CURRENT FLAW DETECTION

CLAIM OF BENEFIT OF PROVISIONAL APPLICATION

Pursuant to 35 U.S.C. §119, the benefit of priority from provisional application 60/253,352, with a filing date of Nov. 28, 2000, is claimed for this non-provisional application.

ORIGIN OF THE INVENTION

The invention described herein was jointly made by an employee of the United States Government and by a contractor during the performance of work under a NASA contract and is subject to provisions of Section 305 of the National Aeronautics and Space Act of 1958, as amended, Public Law 85-568 (72 Stat. 435; 42 USC 2457).

BACKGROUND OF THE INVENTION

Nondestructive evaluation (NDE) technologies have recently been challenged to inspect thick, layered, conducting materials for fatigue and corrosion damage. Structures that fall into this class, such as airframe wings, pose significant difficulties for conventional inspection techniques, and especially challenging is the detection of deeply buried flaws at airframe fasteners. Reflections of ultrasound at layer boundaries cause serious problems for the application of ultrasonic inspection methods. Conventional eddy current inspection techniques are also compromised due to the exponential decay of electromagnetic energy with depth into a conductor.

Eddy current techniques, using detection that is sensitive to the time rate of change of the magnetic field level, are currently the most widely used method for the detection of hidden damage in thin conductors. The sensitivity of the method, however, is severely limited as material thickness increases. Eddy currents decay exponentially with both depth into the material and the square root of the applied frequency. Sufficient field penetration requires the reduction of the excitation frequency. This reduction in frequency, however, limits the sensitivity of the inductive pickup sensor whose output is proportional to the frequency. U.S. Pat. No. 5,648,721, which is hereby incorporated by reference, teaches a flux focusing eddy current probe having separate excitation and pick-up coils, magnetically isolated from one another by a highly permeable flux focusing lens.

The use of Giant Magnetoresistive (GMR) sensors for electromagnetic nondestructive evaluation has grown considerably in the last few years. Technological advances in the research and development of giant magnetoresistive materials has led to commercially available GMR sensors with many qualities well suited for electromagnetic NDE. Low cost GMR magnetometers are now available which are highly sensitive to the magnitude of the external magnetic field, have a small package size, consume little power, and operate at room temperature. Incorporation of these sensors into electromagnetic NDE probes has widened the application range of the field. In particular, the low frequency sensitivity of the devices provides a practical means to perform electromagnetic inspections on thick-layered conducting structures.

There are several other eddy current type methods which use detection sensitive to the magnetic field level as opposed to the time rate of change of the field. Magneto-Optic and Hall sensors are two common techniques. These devices, however, typically require substantial instrumentation and have sensitivities much lower than that of the GMR sensor. Super Conducting Quantum Interface Devices (SQUIDS) have sensitivities better than the GMR devices but the requirement of cryogenic temperatures imposes difficulties in application and typically greatly increases the sensor size. Flux Gate Magnetometers have sensitivities similar to GMR sensors and although they do not require a cryogenic temperature, they do require substantial instrumentation and typically relatively large probe size.

Ultrasonic techniques have been shown to be useful for detecting flaws in thick materials, but have limited success in multilayered structures due to reflection of the wave at the interfaces of the layers. Thermographic techniques have difficulties with metallic and thick materials, and typically require greater amounts of instrumentation for application and data analysis. X-ray methods pose environmental concerns and are not typically portable due to the large instrumentation requirements.

A variety of non-destructive evaluation techniques are currently used to inspect rivet joints, with eddy current testing being the most widely used technique. Several different types of eddy current probes have been developed for the specific purpose of rivet inspection. U.S. Pat. No. 5,648,721, herein incorporated by reference, teaches a probe having a flux focusing lens positioned between an excitation coil and a pick-up coil which are isolated from one another by a flux focusing lens, and a means for rotating the probe about the circular inhomogeneity. The device is very accurate for the detection of near surface fatigue cracks but the performance for deeper inspections is limited due to several features of the design, including flux leakage around the flux focusing lens and decreased detection sensitivity with lowered frequency. Other techniques include a Sliding Probe and a method using pencil probes and templates to trace around the fastener head. The sensititivy of the Sliding Probe is often low and a preferred orientation of the probe may lead to false calls or undetected flaws for rivets which are not aligned in a row. Template methods using pencil probes are very time consuming, and lift off or probe wobble can produce false signals.

OBJECTS

Therefore, it is an object of the present invention to effectively detect flaws in thick conductive materials.

It is a further object of the present invention to effectively detect flaws in multilayer conductive materials.

It is another object of the present invention to provide high sensitivity to low frequency magnetic fields.

It is another object of the present invention to enable the detection of deeply buried flaws.

It is yet another object of the present invention to provide an eddy current probe that is compact in size, operates at room temperature and utilizes simple electronics to provide ease of use and low cost.

It is a further object of the present invention to detect deep flaws about circular fasteners and other circular inhomogeneities in electrically conductive material.

Additional objects and advantages are apparent from the drawings and specification that follow.

SUMMARY OF THE INVENTION

According to the present invention, the foregoing and other objects and advantages are attained by providing a giant magnetoresistive eddy current device that effectively detects deep flaws in thick multilayer conductive materials. The probe uses an excitation coil to induce eddy currents in conducting material perpendicularly oriented to the coil's longitudinal axis. A giant magnetoresistive (GMR) sensor, surrounded by an excitation coil, is used to detect generated fields. Between the excitation coil and the GMR sensor is a highly permeable flux focusing lens which magnetically separates the GMR sensor and excitation coil and produces high flux density at the outer edge of the GMR sensor. The use of feedback inside the flux focusing lens enables complete cancellation of the leakage fields at the GMR sensor location and biasing of the GMR sensor to a location of high magnetic field sensitivity. In an alternate embodiment, a permanent magnet is positioned adjacent to the GMR sensor to accomplish the biasing. Experimental results have demonstrated identification of flaws up to 1 cm deep in aluminum alloy structures.

The present invention is further directed to a magnetoresistive flux focusing eddy current device that effectively detects deep flaws about circular fasteners or inhomogeneities in thick multilayer conductive materials. A giant magnetoresistive flux focusing eddy current device, as described above, is mounted in a hand-held rotating probe assembly that is connected to a computer for system control, data acquisition, processing and storage.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1A:
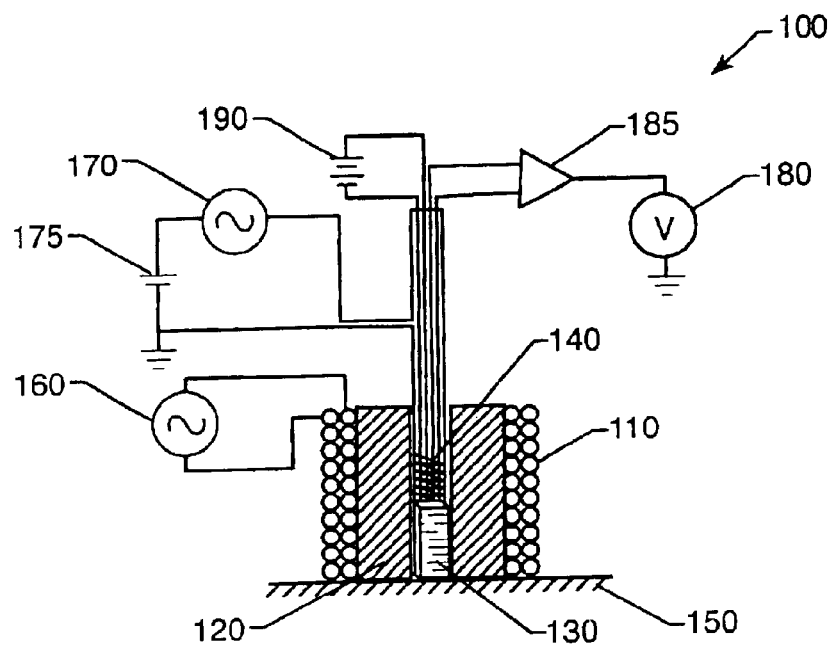
FIG. 1A shows a cross sectional view of a magnetoresistive flux focusing eddy current probe constructed in accordance with the principles of this invention.

With reference now to FIG. 1A, wherein like numbers designate like components throughout all the several figures, the GMR sensor-based flux focusing eddy current probe of the present invention is particularly well adapted for non-destructive evaluation of electrically conductive thick materials having multiple layers and deep cracks. Although particularly useful for such detection, it may also be used effectively for closer-surface flaw detection. The probe generally designated at 100 includes an excitation (drive) coil 110, a flux focusing lens 120, a giant magnetoresistive (GMR) sensor 130, and a feedback coil 140. The probe 100 applies the eddy current principle to evaluate electrically conductive material 150 for faults. An alternating current supplied by a current source 160 electrically connected to the excitation coil 110 produces eddy currents within conductive material 150 placed in proximity with the probe 100. Voltage 190 is supplied to the GMR sensor 130. Magnetic fields created in the GMR sensor 130 generate an electrical potential amplified by a differential preamplifier 185 and registered by an A.C. voltmeter 180 electrically connected to the GMR sensor 130. The flux focusing lens 120 magnetically separates the excitation coil 110 from the GMR sensor 130 and produces high flux density at the edge of the GMR sensor 130. The use of active feedback inside the flux focusing lens 120 enables a complete cancellation of the sinusoidal stray fields at the GMR sensor 130 location. At low frequencies the magnetic flux leakage around the bottom of the flux focusing lens 120 results in a large background signal level. This background signal is removed by applying a feedback signal via feedback source 170 at the same frequency as the current source 160 but 180 degrees out of phase with the GMR sensor 130 output to the feedback coil 140. The feedback coil 140 also shifts the operating point of the GMR sensor 130 out of the low field region where the sensitivity of the probe 100 is low. For this, a D.C. voltage 175 is applied to the feedback coil 140 to provide a sufficient static background field level to bias the GMR sensor 130 in the linear region.

Figure 1B:
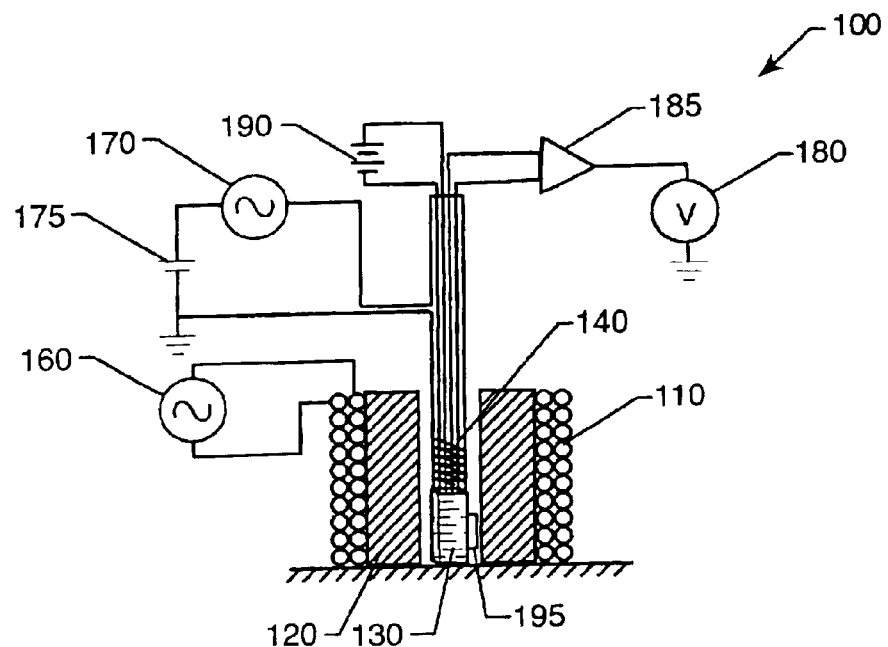
FIG. 1B shows an alternate embodiment of the probe having a permanent magnet for biasing.

In an alternate embodiment, a permanent magnet 195 is positioned on the substrate directly behind the GMR sensor 130, as illustrated in FIG. 1B. The permanent magnet 195 is used to provide a sufficient D.C. bias to the sensor to keep the device in the linear response region. The feedback coil 140 is then used solely for A.C. feedback, rather than both sensor biasing and A.C. feedback. The incorporation of the permanent magnet 195 greatly reduces field generation requirements of the feedback coil 140, enabling construction of a smaller device with lower power requirements. A D.C. bias from approximately 0.5 Oersted to approximately 0.75 Oersted was used in the experimental examples discussed herein.

Electromagnetic inspection of thick conducting materials requires a low frequency excitation due to the skin depth relationship, which is given in CGS units by $$B_z = B_0 \exp(-z/\delta) \quad (1)$$

$$\delta = c/\sqrt{2\pi\mu\omega\sigma} \quad (2)$$

where $B_z$ is the magnetic field at depth z into the material under test, $B_o$ is the magnetic field at the surface, c is the speed of light, $\mu$ is the permeability, $\omega$ is the angular frequency, $\sigma$ is the conductivity, and $\delta$ is the skin depth. The skin depth of a highly conducting material will be quite small unless the frequency of operation is also lowered. In aluminum alloys typically used in airframe construction with $\mu=1$ and $\sigma=1.7\times10^{17}$ sec$^{-1}$, for example, a frequency of 130 Hz is required for the skin depth to reach 1 centimeter into the material under test. At such frequencies, pickup coil type sensors lose sensitivity due to Faraday's law of electromagnetic induction that states $$\varepsilon = -\frac{A}{c}\frac{dB}{dt} \propto \omega \sin \omega t \quad (3)$$

The electromotive force, $\varepsilon$, induced around a circuit is proportional to area enclosed, A, times the time rate of change of the magnetic field through the circuit. As the excitation frequency is lowered, the induced voltage across the pickup coil is reduced, reducing the effectiveness of the inspection.

Giant magnetoresistive sensors respond to the magnitude of the external field instead of the time rate of change of the field and therefore do not lose sensitivity at low frequencies. In the absence of an applied field, the resistivity of the GMR sensor is high due to scattering between oppositely polarized electrons in the antiferromagnetically coupled multi-layers of the device. An external field aligns the magnetic moments of the ferromagnetic layers, eliminating this scattering mechanism and thereby reducing the resistivity of the material. A schematic diagram of a commercially available GMR sensor 130 is displayed in FIG. 2. The design uses four GMR elements 210 connected in a Wheatstone bridge configuration. Two elements with shielding 220 are shielded from the external field. In the absence of an external field, all four elements will have the same resistance and no voltage will be detected across the center of the bridge. When an external field is present, the resistivity of the two unshielded GMR elements will drop and a positive voltage will be detected across the bridge. The four GMR elements 210 along with the flux concentrators 230, which increase the sensitivity of the sensor, are packaged in an eight pin integrated circuit chip. Alternatively, the GMR sensor 130 can be incorporated into the probe 100 in its unpackaged die form. This form may be preferred if smaller sizes are desired. The die form of the GMR sensor 130 can be used with both embodiments of the active feedback discussed earlier.

Figure 2:
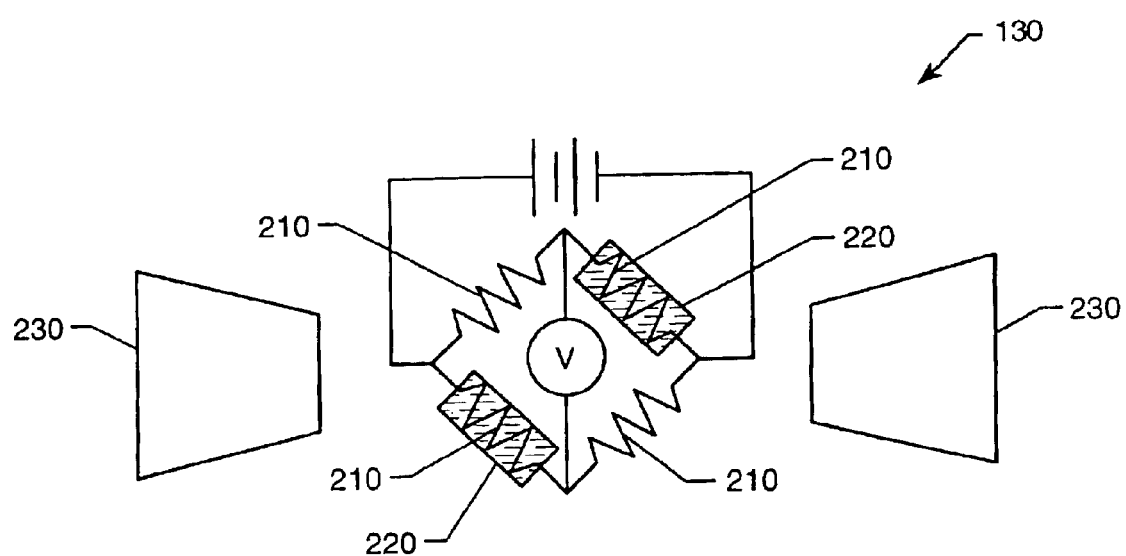
FIG. 2 shows a schematic of a commercially available GMR sensor.
Figure 3:
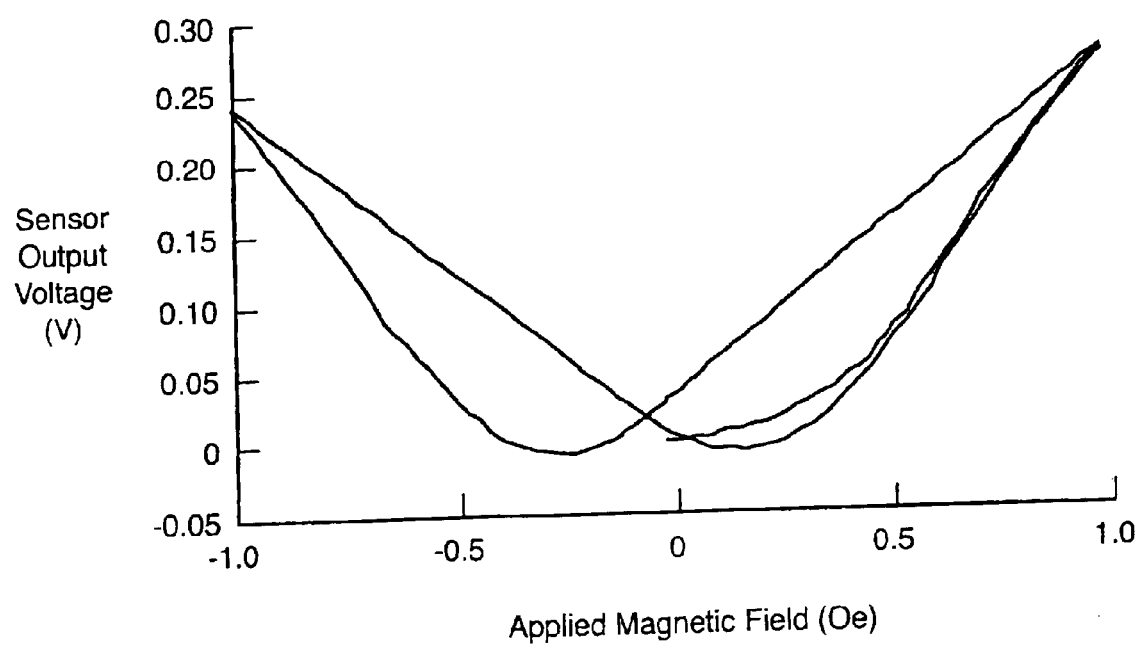
FIG. 3 shows calibration data for the GMR sensor depicted in FIG. 2.

FIG. 3 shows the calibration data for GMR sensor 130 of FIG. 2. This data was acquired with the GMR sensor 130 placed in the center of a Helmholtz pair driven by a precision current source. Fifteen volts were placed across the GMR bridge, and a 20 dB differential preamplifier was used to amplify the output voltage of the GMR sensor 130. The output increases with the magnitude of the magnetic field and the sensitivity, the slope of the output voltage versus applied field, drops dramatically in the low field region between approximately ±0.5 Oe. GMR sensors are available in various ranges and sensitivites. Their selection is based on the desired size and voltage response per field change for particular flaw measurements.

With further reference now to FIGS. 1A and 1B, the excitation coil 110, the flux focusing lens 120, and the GMR sensor 130 are concentrically arranged with the excitation coil 110 at the exterior of the probe 100, the GMR sensor 130 at the innermost position of the probe 100, and the flux focusing lens 120 between the excitation coil 110 and the GMR sensor 130. The overall size of the probe 100 is primarily determined by the diameter of the flux focusing lens 120, which is a function of fault depth and fault isolation accuracy, and the size of the GMR sensor 130. The diameter of the lens 120 is minimized to reduce the overall size of the probe 100 and to provide accurate location information of identified faults, though it must be of sufficient size to support test frequencies of the applied current from the current source 160 and to maximize search area covered by the probe 100. Likewise, the thickness of the lens 120 is minimized to ensure energy created by the magnetic field of the excitation coil 110 produces energy in the GMR sensor 130 when the probe 100 is in free space or a flaw in the conductive material 150 crosses the boundary established by the lens 120, though the lens 120 must provide isolation from direct magnetic energy of the excitation coil 110 from producing an alternating current in the GMR sensor 130 when the probe 100 is in contact with unflawed conductive material 150. Direct energy transfer is avoided when the lens 120 thickness is several times the skin depth of the magnetic flux within the lens 120. Generally, a lens 120 wall thickness of at least three skin depths and a sensor 130 height less than the half height of the lens 120 is desired.

An alternating current 160 applied to the excitation coil 110 creates a magnetic field which in turn creates eddy currents within conductive material 150. The depth of penetration of the magnetic field into the test material 150 is dependent upon the conductivity of the material 150 and the frequency of the applied current source 160. Consequently, the frequency of the drive signal is predetermined by the type of inspection being performed, with inspection for deeper flaws requiring lower frequencies.

The magnetic field is also established in the flux focusing lens 120. The lens 120 is formed of conducting material high in magnetic permeability which provides a low reluctance path to divert the magnetic field away from the GMR sensor 130. The point of maximum penetration of the concentrated magnetic field within the lens 120 is at one half the height of the excitation coil 110. In the preferred embodiment, the top of the GMR sensor 130 falls below this maximum penetration point.

In the absence of a conducting material test sample 150, some leakage of the magnetic flux around the lens 120 results. The leakage flux produces a potential in the GMR sensor 130 which provides a signal to the A.C. voltmeter 180. When the probe 100 is placed above a non-flawed electrically conductive surface, however, a complete electromagnetic separation of the GMR sensor 130 from the excitation coil 110 can be achieved. The flux is concentrated within the conductive sample 150 and generates eddy currents. The induced eddy currents work to stop any change in the magnetic state of the system so that the leakage field within the interior of the flux focusing lens 120 is canceled, resulting in a null signal to the A.C. voltmeter 180.

In the presence of a conductive material fault that divides the area covered by the probe 100, a change in eddy current flow results. The field produced by the eddy currents pass through the area of the GMR sensor 130 resulting in a potential being established across the GMR sensor 130. This provides an unambiguous voltage signal as indicative of the presence of a conductive material fault.

Figure 4:
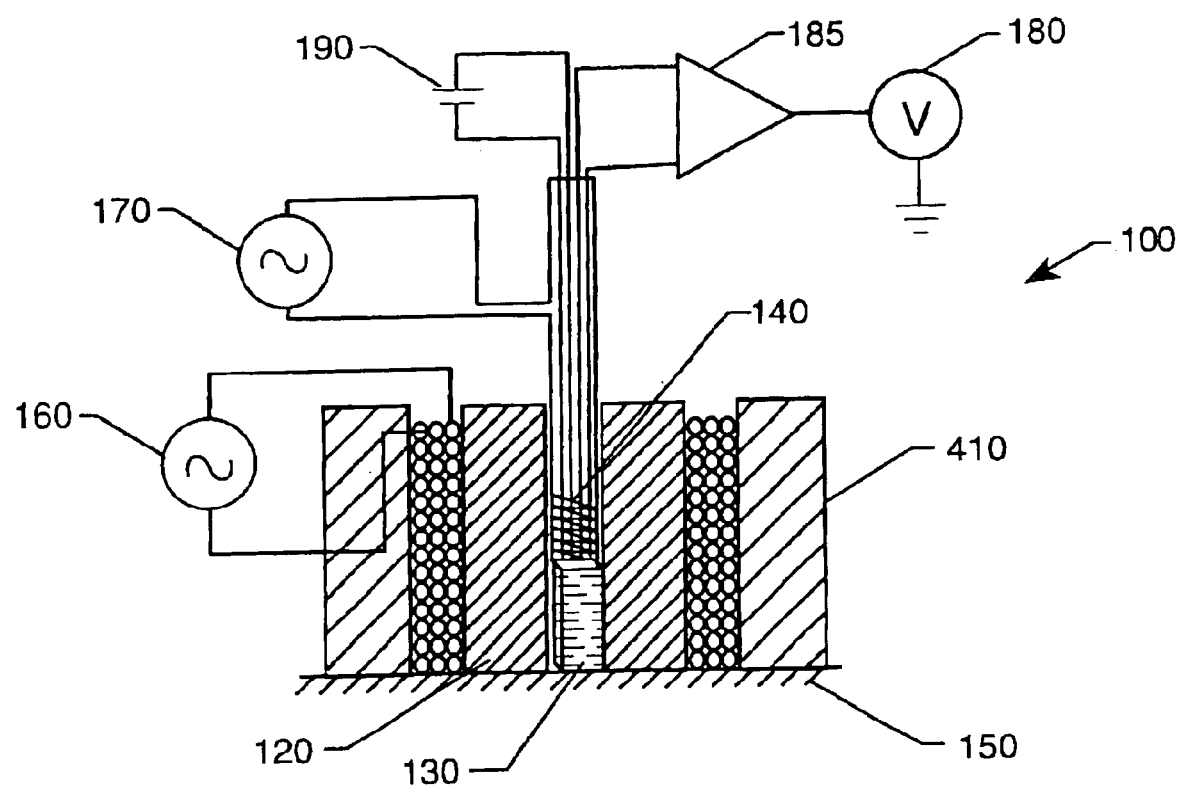
FIG. 4 shows an alternate embodiment of the magnetoresistive flux focusing eddy current probe for detecting faults close to an edge.

With reference now to FIG. 4, an alternate probe configuration supports detecting faults close to an edge of the conductive material 150 under test or near other conductive material discontinuities. An exterior shield 410 made of conductive material high in magnetic permeability focuses magnetic flux around the outside edge of the probe to prevent eddy currents from reflecting off a nearby conductive material edge and into the area of the GMR sensor 130. This allows the probe 100 to be used near conductive material edges, but reduces the probe's overall sensitivity performance.

Figure 5A:
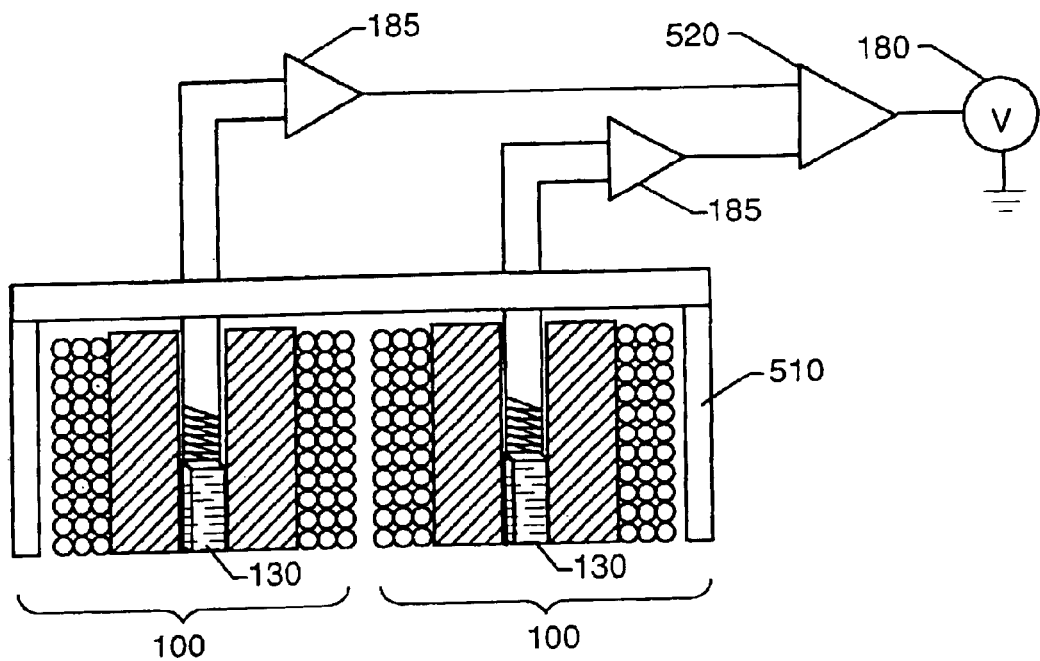
FIG. 5A shows an alternate embodiment of the magnetoresistive flux focusing eddy current probe that provides additional resistance to lift-off.
Figure 5B:
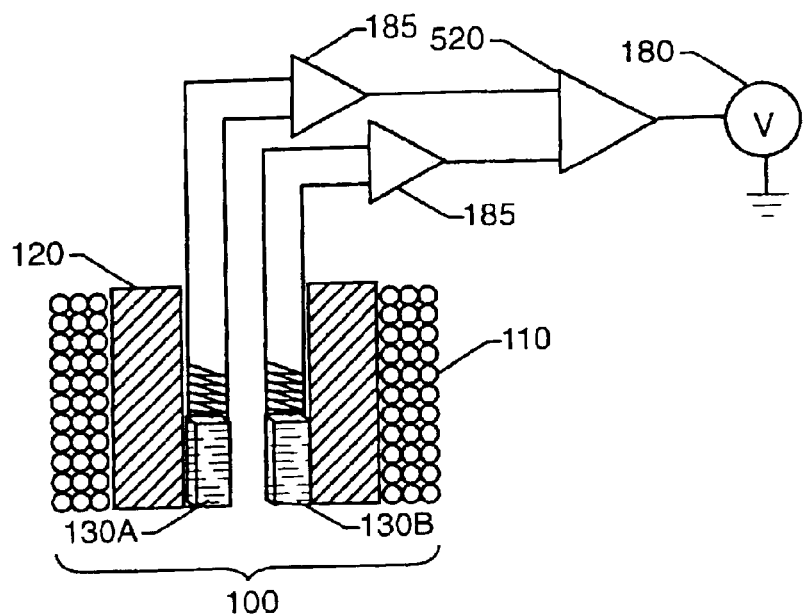
FIG. 5B shows a further alternate embodiment of the magnetoresistive flux focusing eddy current probe that provides additional resistance to lift-off.

With reference now to FIGS. 5A and 5B, alternate probe configurations are possible which provide further protection from lift-off conditions incorrectly indicating the presence of a conductive material fault. Signals from a plurality of probes 100 combined within a casing 510, illustrated in FIG. 5A, or a plurality of GMR sensors 130A and 130B within a single excitation coil 110 and flux focusing lens 120, illustrated in FIG. 5B, are compared to one another. Equal, non-zero signal levels signify probe lift-off from the test material. GMR sensors 130 or 130A and 130B are electrically connected to differential amplifiers 185 and 520. Lift-off conditions result in equal signal level outputs such that the difference is zero and no fault indication is provided by the A.C. voltmeter 180.

Figure 6A:
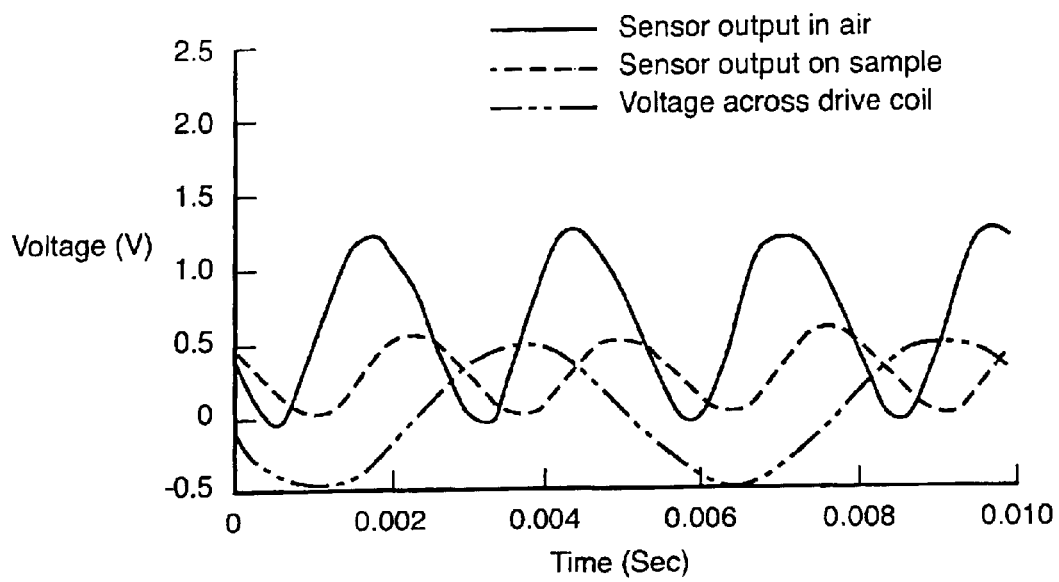
FIG. 6A shows excitation coil and GMR sensor output waveforms for the magnetoresistive flux focusing eddy current probe, without feedback to the GMR sensor, for a 185 Hz drive with 15 volts to the GMR bridge and 40 dB preamplification when the probe is in contact with a conductive sample.
Figure 6B:
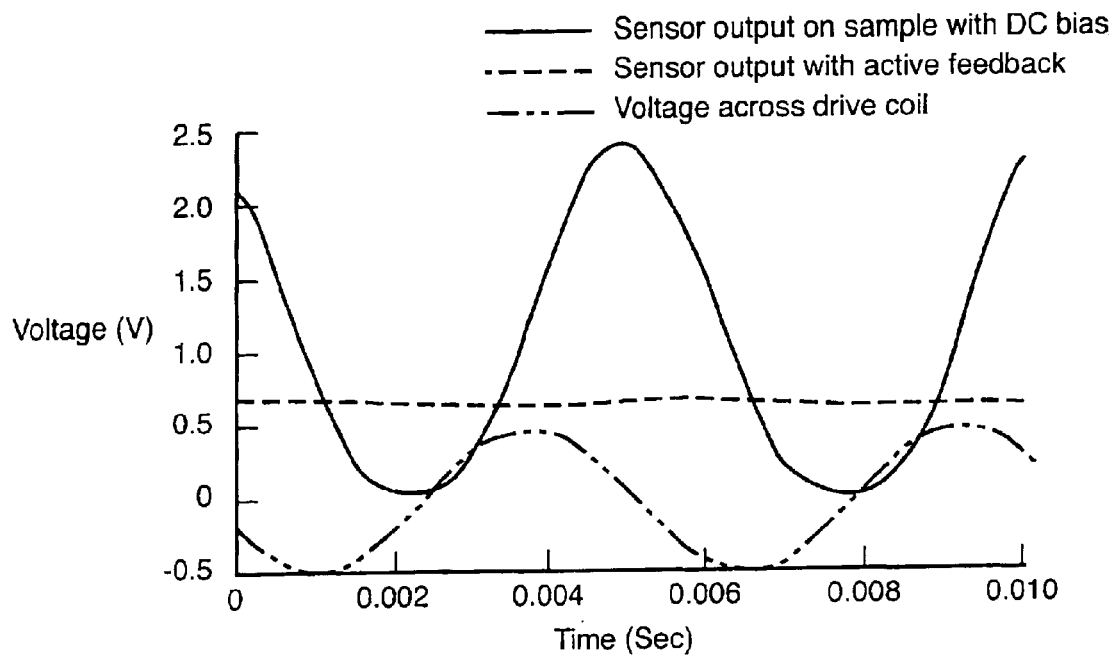
FIG. 6B shows the change in GMR sensor output as the feedback source is adjusted.

FIGS. 6A and 6B display the excitation coil 110 and GMR sensor 130 output waveforms at various stages of feedback to the GMR sensor 130. The data were acquired at 185 Hz drive from current source 160 with 15 volts from D.C. voltage source 190 to the GMR bridge and 40 dB preamplification 185. The waveforms in FIG. 6A were taken without any feedback. The output signal is rectified due to the insensitivity of the GMR sensor 130 to the direction of the applied field. A significant drop in the output voltage is observed when the probe is placed on the conducting sample 150, although a relatively large output voltage is still observed.

FIG. 6B displays the change in the output as the feedback is adjusted. With the probe 100 on a sample 150, the application of a D.C. bias from D.C. voltage source 190 to the feedback coil 140 shifts the operating point of the sensor away from the zero crossing area and up the calibration curve to a location of higher sensitivity. This results in an increased output amplitude of the GMR sensor 130. Also, the signal is now at the same frequency as the current source 160, with the rectification of the signal eliminated. The final step is then to apply a sinusoidal signal from the feedback source 170 to the feedback coil 140 at the excitation coil 110 frequency but 180° out of phase with the GMR sensor 130 output. The resulting output is a D.C. shifted amplitude with only a very small A.C. component. Adjusting the feedback in this manner cancels the leakage magnetic fields in the center of the probe and biases the GMR sensor 130 in order to obtain maximum sensitivity to small changes in the magnetic field caused by deeply buried defects.

Once the feedback source 170 is adjusted as described above and illustrated in FIG. 6B, the sample 150 under test can be scanned. Lock-in amplifier 185 referenced to the excitation coil 110 is used to record both the amplitude and phase of the probe output as a function of position on the sample 150 surface.

Figure 7A:
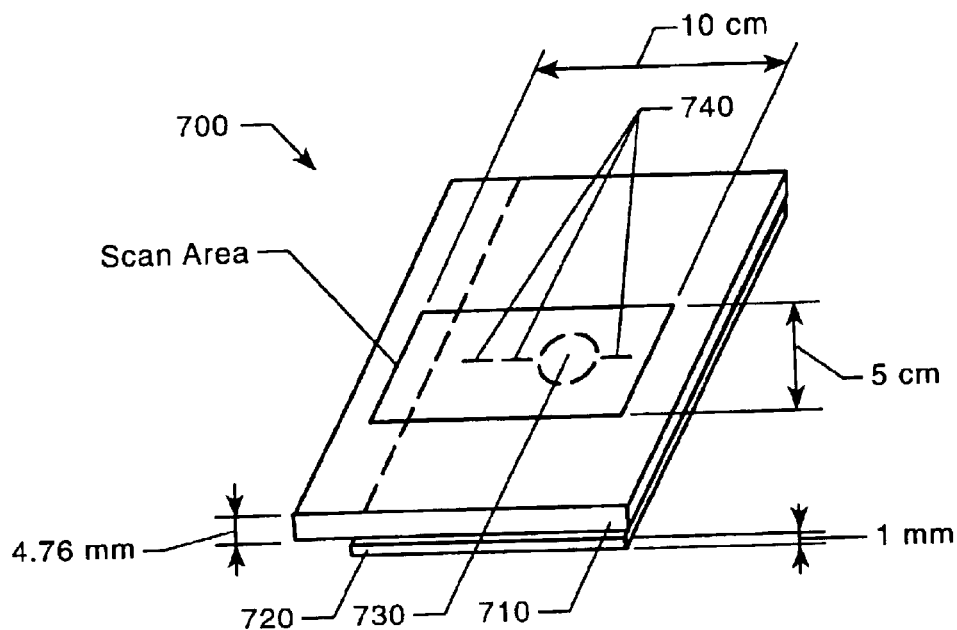
FIG. 7A shows a two-layer aluminum alloy test sample having a 4.76 mm thick unflawed top layer and a 1 mm thick lower layer having fatigue cracks grown from either side of a drilled center hole.
Figure 7B:
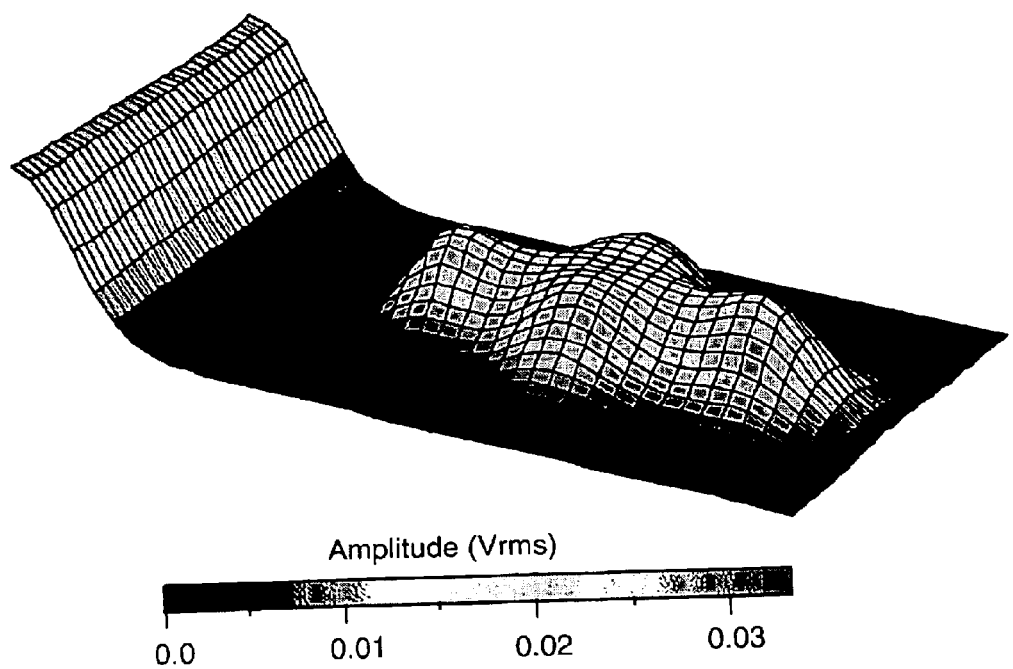
FIG. 7B shows the geometry and surface plot of the experimentally measured probe output amplitude for the FIG. 7A sample.

FIG. 7B shows experimental results from the test of a two-layer aluminum alloy lay-up 700 shown in FIG. 7A. Referencing FIG. 7A, the top layer 710 was formed of an unflawed 4.76 mm thick aluminum alloy plate. The lower layer 720 was formed from a 1 mm thick aluminum alloy plate with fatigue cracks 740 grown from either side of a drilled center hole 730. The sample was scanned from the unflawed side with the probe operating at 375 Hz.

FIG. 7B displays the geometry and a surface plot of the experimentally measured probe 100 output amplitude for the sample. The edge of the bottom plate 720, center hole 730, and fatigue cracks 740 emanating from either side of the hole 730 are all clearly visible in the surface plot. In addition, a peak in the output amplitude at the location of the fatigue crack tips is evident in the data.

Figure 8A:
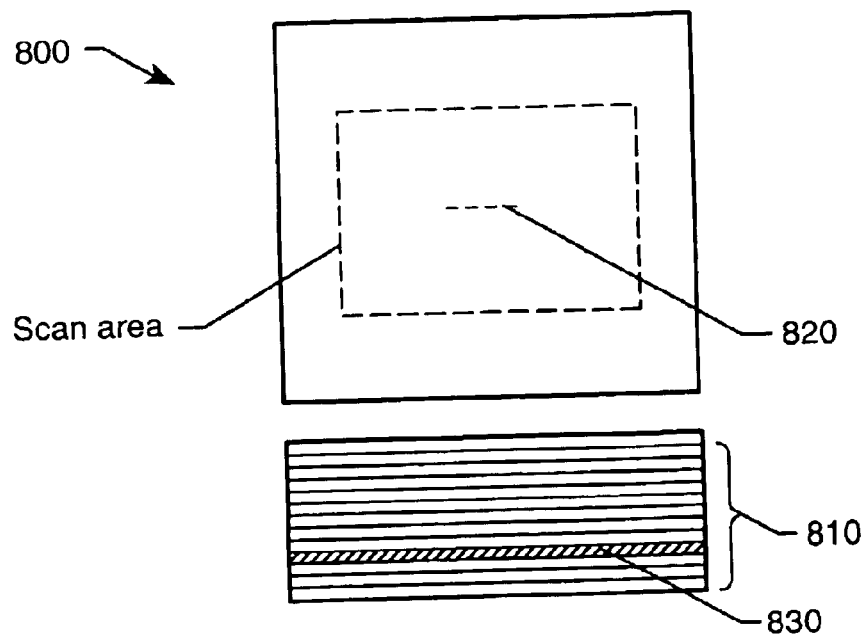
FIG. 8A shows a 13-layer aluminum test sample having a flaw in the 10th layer, beneath 9 mm of unflawed aluminum.

A second experimental sample 800, shown in FIG. 8A, was fabricated to examine the detection capabilities of the probe 100 for flaws at varying depths in thick layered conductors such as airframe wings. A set of thirteen, 1 mm thick, aluminum plates 810 with a net cross section of 15×15 $cm^2$ was obtained. An EDM notch 820 of 1.4×0.0127 $cm^2$ was placed in the center of one of the plates. The location of this flawed layer within the stack of unflawed plates could then be varied, and data acquired over the flawed area for each case. Results using the probe 100 without the feedback coil 140 showed that the flaw could be clearly detected in the $6^{th}$ and $7^{th}$ layer, but that the signal to noise ratio dropped dramatically for deeper layers. The plotted data 860 were acquired at an operating frequency of 185 Hz with the flaw 820 placed in the $10^{th}$ layer 830 of the sample 800, beneath 9 mm of unflawed aluminum. The flaw location 820 is clearly imaged in the experimental data. A double peak indication is detected since the notch length of 1.4 cm was less than the outside diameter of the GMR based probe (1.9 cm). A peak in the output is observed when the probe is centered over either tip of the flaw 820. When the probe is centered over the midpoint of the notch, however, the majority of the induced current will flow unperturbed around the flaw tips.

Figure 8B:
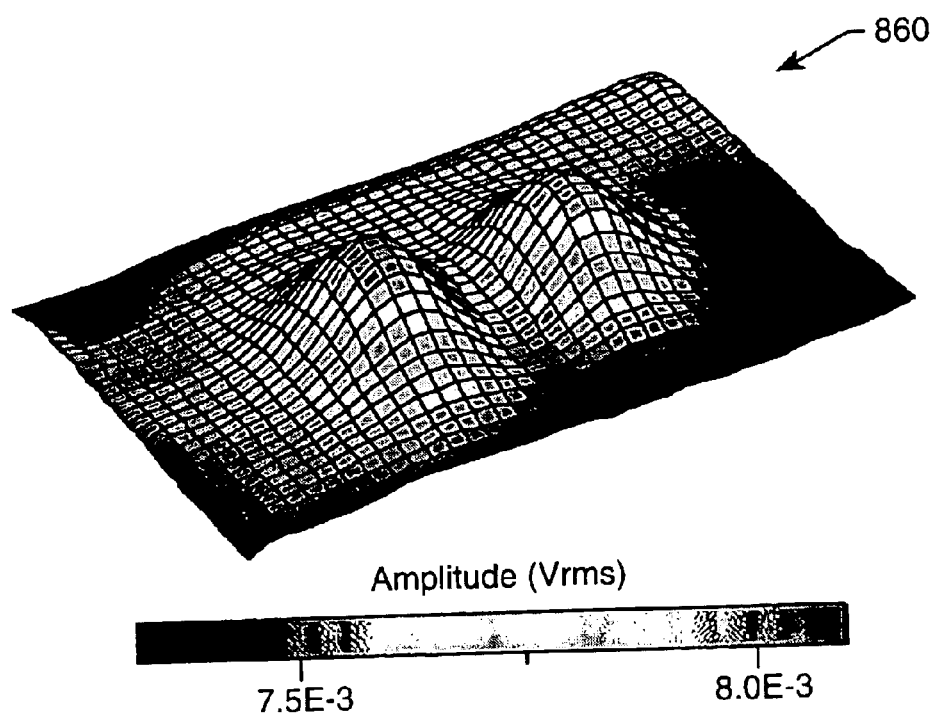
FIG. 8B shows the geometry and surface plot of the experimentally measured probe output amplitude for the FIG. 8A sample.

The results shown in FIG. 8B for the $10^{th}$ layer flaw were achieved by using additional data analysis and image processing that were not required for shallower flaws such as those depicted in FIG. 7A. In FIG. 7A the amplitude of the probe output voltage was used to identify the flaw location. In FIG. 8A, however, the amplitude data was combined with the phase information in order to obtain a phase rotated amplitude. The probe output voltage was calculated as $$V_{out}=A\cos(\phi+\beta) \quad (4)$$

were $V_{out}$ is the probe output voltage, A is the root mean square output amplitude, 100 is the phase of the output waveform with reference to the drive signal, and $\beta$ is a constant phase shift applied uniformly to all data points. The phase shift is rotated so as to minimize output voltage changes due to lift-off effects and maximize the signal due to the deeply buried flaws. The method is very similar to the standard eddy current practice of rotating the impedance plane diagram so as to provide a horizontal signal for lift-off variations and then monitoring the vertical component of the change in impedance.

Figure 9A:
FIG. 9A shows the sensor output amplitude for a 1 cm deep flaw for the sample of FIGS. 8A and 8B.
Figure 9B:
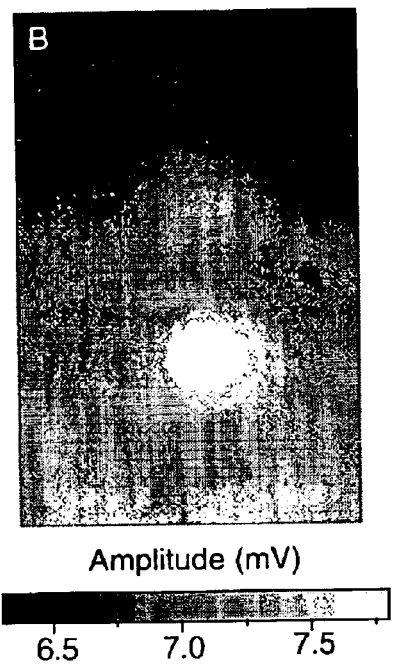
FIG. 9B shows the subsequent phase rotated output amplitude of FIG. 9A.
Figure 9C:
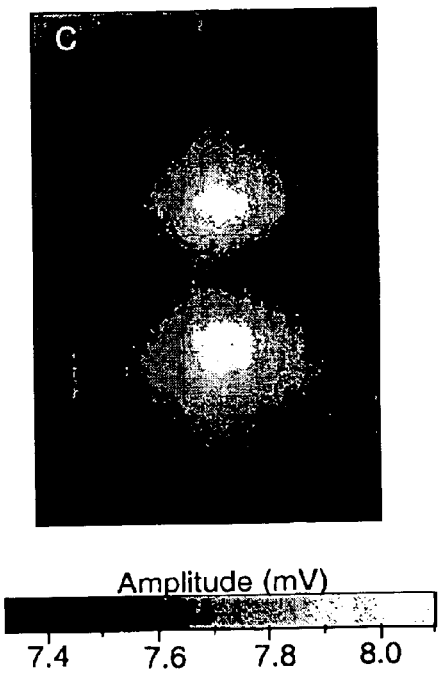
FIG. 9C shows the flattened image of FIG. 9B.
Figure 9D:
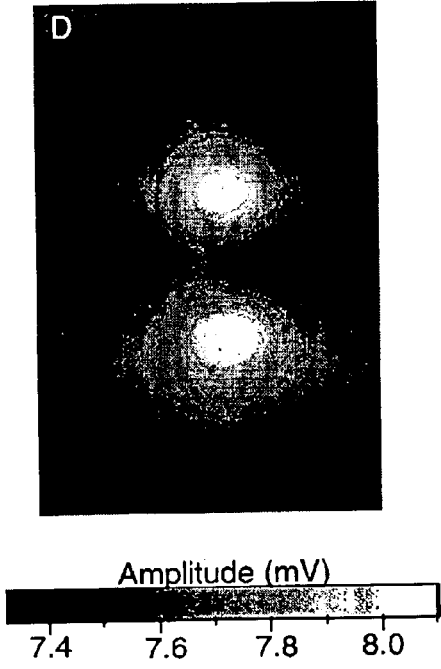
FIG. 9D shows the low pass filtered data of FIG. 9C.

After the amplitude and phase data were combined, a simple image processing routine was used to enhance the image quality for greater flaw detectability. The image was first flattened, in order to remove any linear drift in the data caused by the presence of a small angle between the scanning plane and the sample surface or electronics drift during the scan. A low pass two-dimensional Fourier filter was then applied across the sample set in order to remove any high frequency noise caused by the scanning system. FIGS. 9A through 9D detail the data analysis and image processing steps as applied to the data presented in FIG. 8B. FIG. 9A shows the GMR sensor output amplitude, FIG. 9B shows the phase rotated amplitude, FIG. 9C shows the flattened image and FIG. 9D shows the low pass Fourier filtered amplitude.

Figure 10:
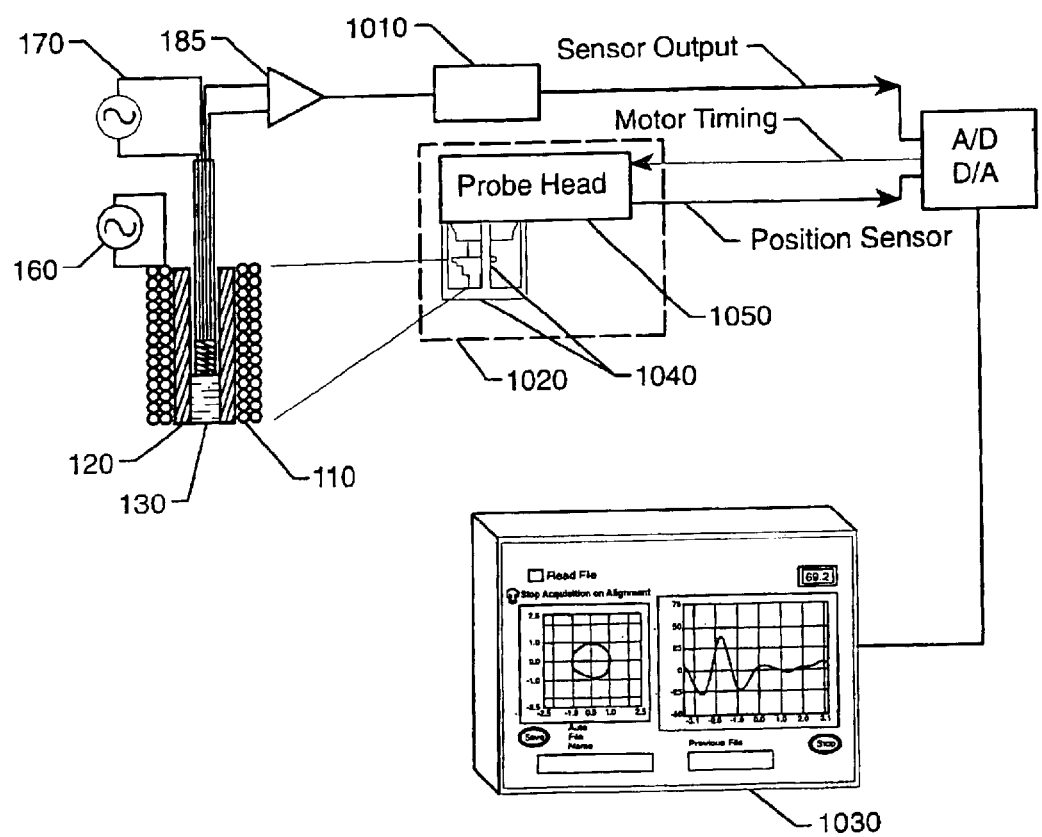
FIG. 10 shows a schematic diagram of the rotating probe embodiment.

Another embodiment of the present invention, shown schematically in FIG. 10, supports detecting deep flaws about any circular fastener such as rivets, or about circular inhomogeneities. Sensor 130 output is amplified 185 and read by peak to peak detector 1010. The sensor 130 output is monitored as the probe is scanned about the circumference of the fastener. Scanning is performed through stepper motor control with a typical scan frequency of 3 Hz. Spatial Fourier filtering applied to the probe output is then used to highlight voltage variations caused by the presence of fatigue cracks as well as to provide feedback on the rotation center for probe alignment. The total system gain is approximately 52 dB.

Maintaining a constant distance between the probe center and rivet center enables the signal due to the current flow about the rivet to be held constant. Any further changes in the current distribution, such as that due to a fatigue crack at the rivet joint, can then be detected as an increase in the output voltage above that due to the flow about the rivet head. In addition, the high current density at the location along the rivet circumference where the radius vector is along the line joining the rivet and probe centers enhances the flaw detection capabilities of the probe over that of an isolated flaw.

The probe is positioned a fixed radial distance from the center of the rivet and peak to peak detector 1010 measures the amplified voltage as the circumference of the rivet is traversed. Any suitable means, shown generally as rotation assembly 1040, may be used to rotate the probe at a constant distance from the center of the rivet or circular inhomogeneity. For example, as described in U.S. Pat. No. 5,648,721, the probe 100 may be placed on a rotator comprising a pivot leg positioned at the center of a fastener, with the pivot leg connected to an arm that supports the probe 100 as it circles the fastener and passes over a crack.

Figure 11:
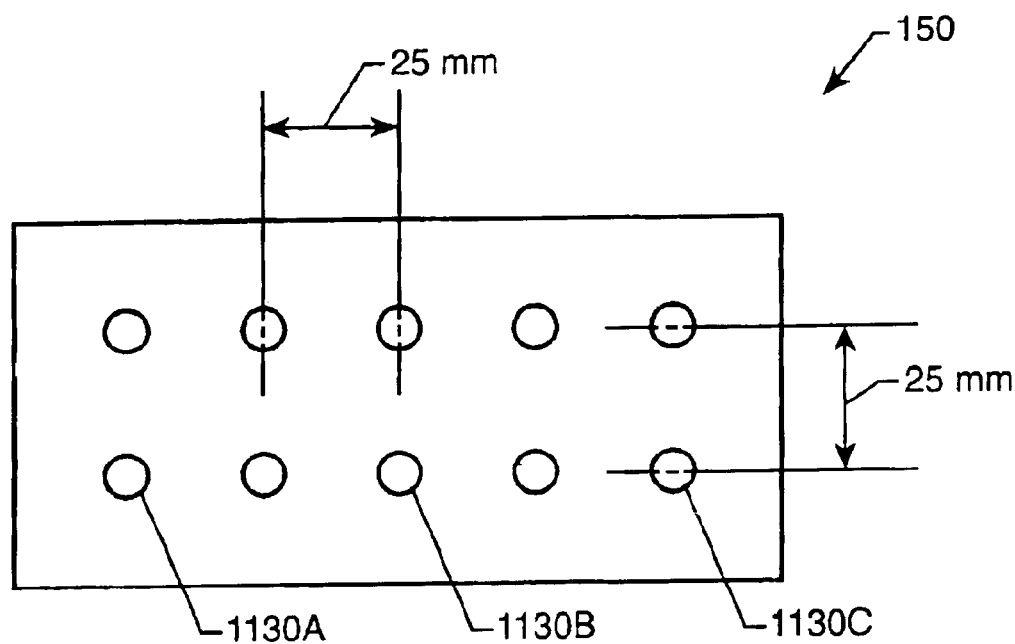
FIG. 11 shows a multilayer experimental sample used for the rotating magnetoresistive flux focusing eddy current probe embodiment.
Figure 11:
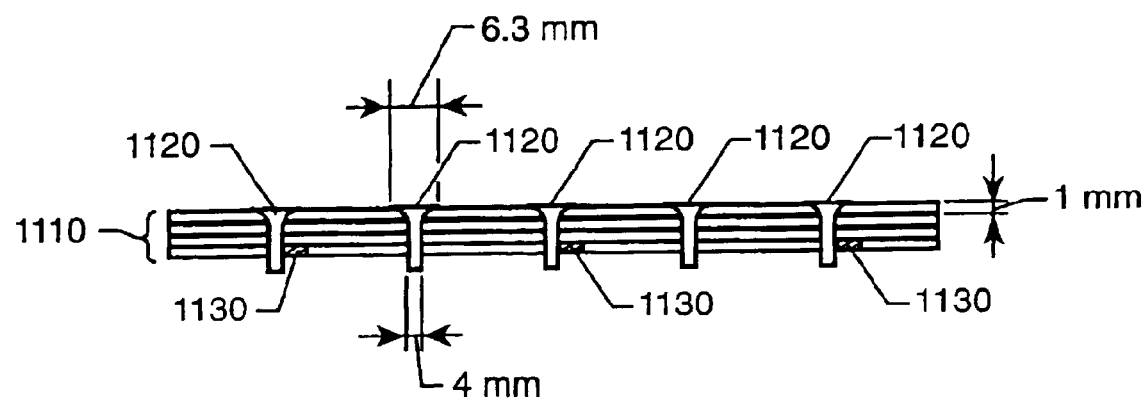

The flaw detection capabilities of the rotating embodiment were examined experimentally using a riveted multilayer aluminum sample. As pictured in FIG. 11, the sample 150 consisted of a set of 1 mm thick Aluminum 2024 plates 1110. The top plate was drilled and countersunk for 4 mm 100° rivets 1120. EDM notches 1130 of lengths 1.5, 2.5, and 3.8 mm were machined at the rivet holes in the flawed layer. The rivet pattern was drilled into three additional plates that could be added to the sample layup, increasing the depth of the flawed layer. Nonmagnetic fasteners were attached to the bottom of the threaded rivets in order to secure the sample layers.

Figure 12A:
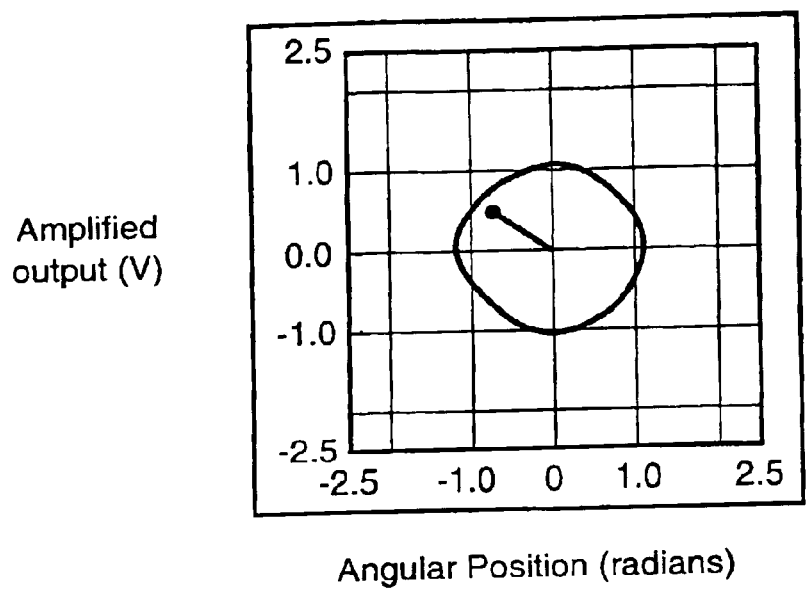
FIG. 12A shows amplified output for a 2.5 mm third layer flaw.
Figure 12B:
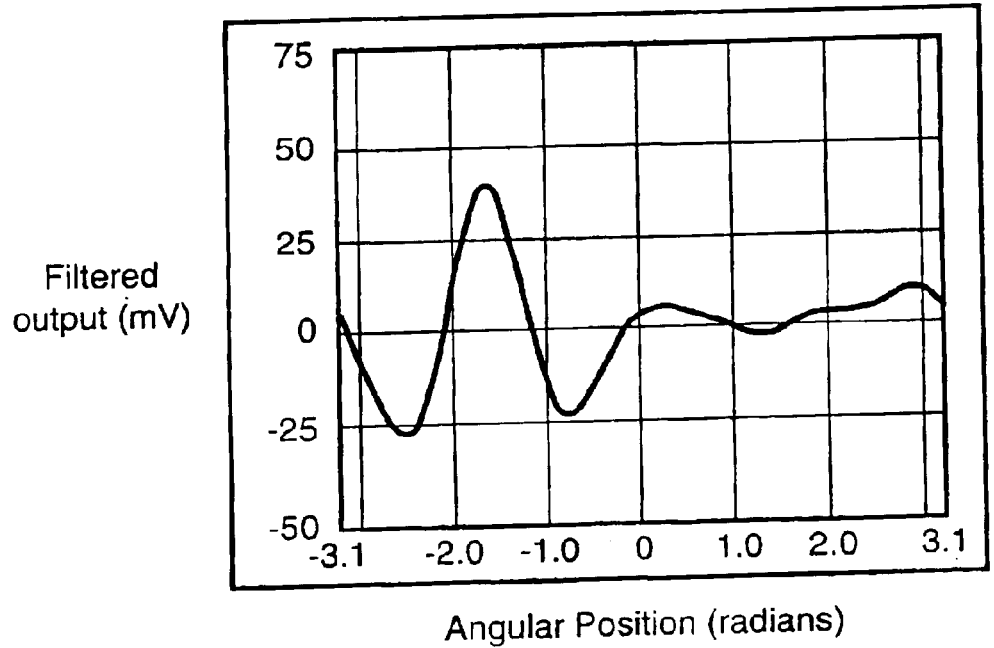
FIG. 12B shows filtered output corresponding to FIG. 12A.
Figure 13A:
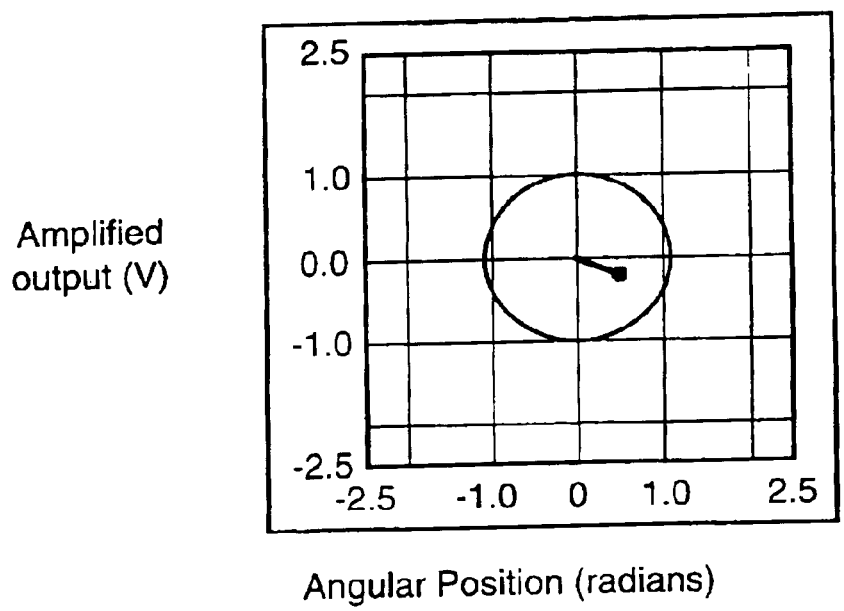
FIG. 13A shows amplified output for an unflawed rivet joint in a three layer sample.
Figure 13B:
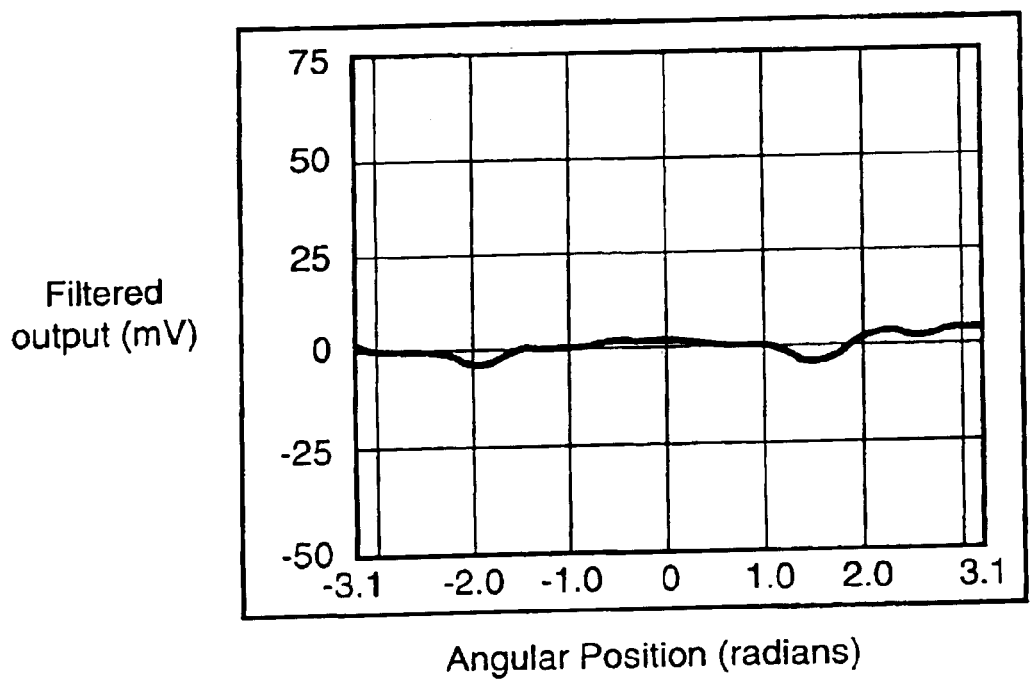
FIG. 13B shows filtered output corresponding to FIG. 13A.

FIGS. 12A and 12B show the panel displays for inspection of a third layer 2.5 mm EDM notch. FIG. 12A displays a polar plot of the amplified probe output voltage during a scan about the fastener. FIG. 12B shows the spatial Fourier filtered signal in millivolts versus the angular position in radians. The flaw is clearly visible as a high amplitude oscillation at −1.5 radians. FIGS. 13A and 13B display the results for a scan of an unflawed rivet joint in the three-layer sample. Data are acquired as the probe rotates about the fastener. A rotation frequency of 2.5 Hz was used such that a complete scan was acquired in 0.4 seconds. The amplified output voltage is nearly constant at 1 volt in both FIGS. 12A and 13A. A slight increase in the raw data is observed at the 9:00 position in FIG. 12A, corresponding to the location of the third layer flaw. A background signal caused by the varying magnetic field around the stepper motor is also observed. The twelve pole pairs of the permanent magnet rotor within the motor produce a cyclic field variation with 12 cycles per revolution. The specifications of the peak to peak detector were selected to eliminate most of the effects of this variation. The drive signal 160, although low frequency, is much higher than the 30 Hz signal due to the stepper motor magnets (12 cycles/revolution×2.5 revolutions/second). The peak to peak circuit then measures $V_{p-p}$ of the drive signal. Only a small distortion due to the stepper motor field remains. This distortion is manifested as a twelve-sided polygon in the background of the polar plots.

FIGS. 12B and 13B display the filtered results in units of millivolts versus radians. For these results, a band pass spatial Fourier filter around the predicted flaw frequency is applied to the data. The spatial Fourier filter is described in Wincheski, B., Fulton, J., Todhunter, R., Simpson, J., 1996, *Review of Progress in Quantitative NDE*, Plenum Press, 2133, herein incorporated by reference. The filter removes the large D.C. background and minimizes the stepper motor effects described above as well as other anomalies such as rivet tilt or misfit. The resulting display clearly identifies the 2.5 mm third layer flaw and produces a nearly flat background for the unflawed sample. The peak amplitude of the flawed signal is 38.8 mV, as compared to 2.4 mV for the unflawed sample. This peak output voltage is recorded and compared to the value of a predetermined threshold for impartial flaw identification.

The flaw detection capabilities for various flaw depths are summarized in Table 1. The operating frequency was set at 1.5, 1.3 and 0.9 kHz for third, fourth, and fifth layer inspections, respectively.

Figure 14:
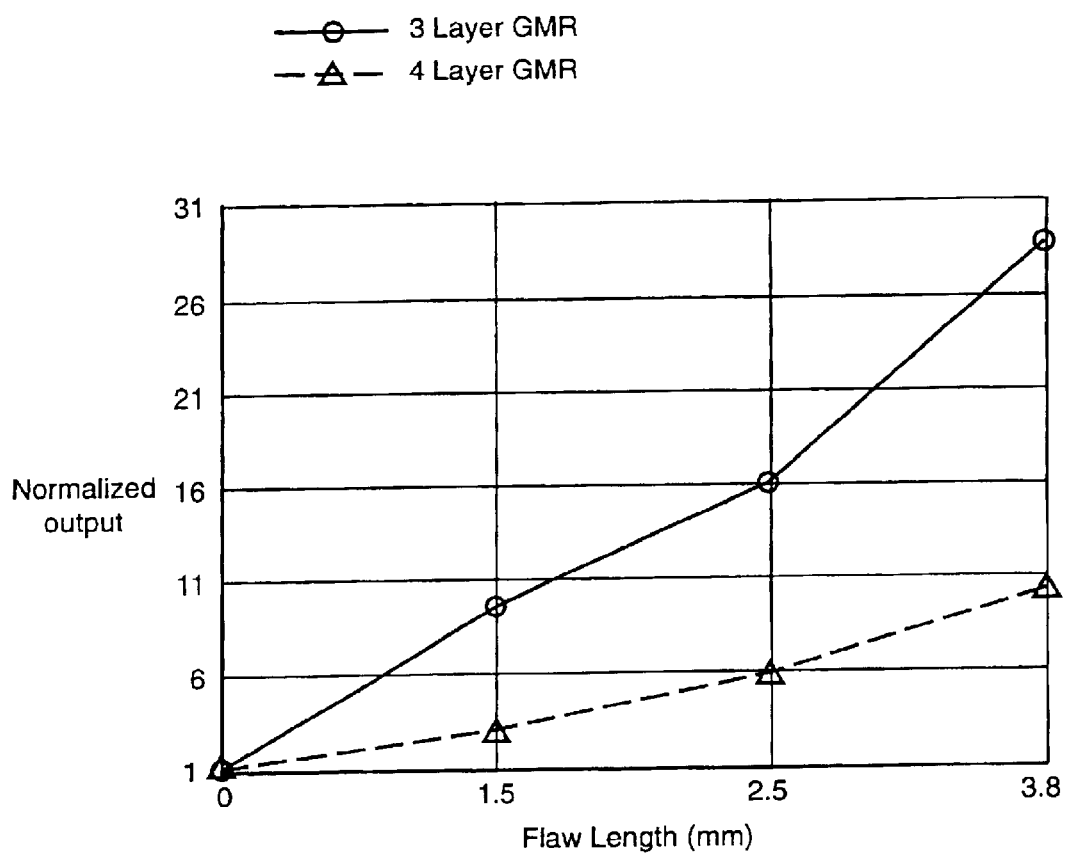
FIG. 14 shows rotating probe outputs normalized to inspection results for an unflawed fastener.

A plot of the filtered output probe voltage versus flaw length for the three and four layer samples is displayed is FIG. 14. The data is normalized to the peak amplitude for the scan of an unflawed rivet. The 1.5 mm and 2.5 mm flaws in the fifth layer were not detectable above the background.

TABLE 1

| Flaw Layer | Unflawed Fastener | 1.5 mm Flaw | 2.5 mm Flaw | 3.8 mm Flaw |
|---|---|---|---|---|
| Third | 2.4 mV | 23.3 mV | 38.8 mV | 69.2 mV |
| Fourth | 2.2 mV | 6.9 mV | 13.3 mV | 22.8 mV |
| Fifth | 2.1 mV | — | — | 7.9 mV |

In another embodiment of the rotating probe, a permanent magnet is positioned on the substrate directly behind the GMR sensor, as described earlier.

Figure 15:
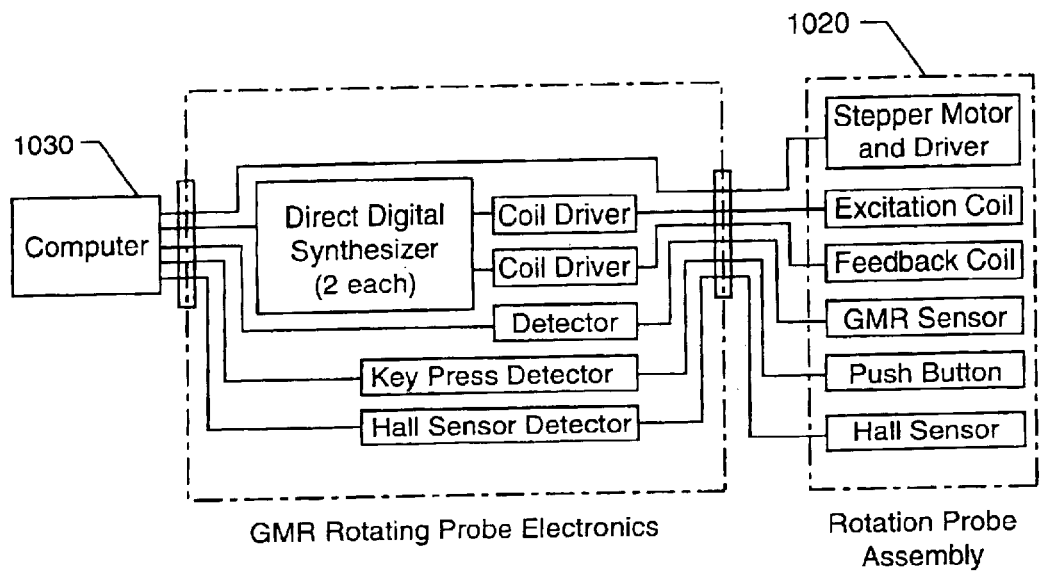
FIG. 15 shows circuitry for the rotating probe.

FIG. 15 illustrates system electronics for the embodiment of the rotating probe having a permanent magnet for D.C. biasing. Two synchronized direct digital synthesis chips give full computer 1030 control of the amplitude, frequency, and phase angle of the source signals (feedback source 170 and current source 160) to the excitation 110 and feedback 140 coils. This level of programming control allows for the proper nulling field to the GMR sensor 130, and is an alternative to the manual method described earlier. In particular, the relative phase angle between the two sources is directly related to the inspection depth by the skin depth equation, given in CGS units by:

$$B_z = B_0 \exp(-z/\delta)\exp(iz\delta - i\omega t) \quad (5)$$

$$\delta = c/\sqrt{2\pi\mu\omega\sigma} \quad (6)$$

where $B_z$ is the magnetic field at depth z into the material under test, $B_0$ is the magnetic field at the surface, c is the speed of light, $\mu$ is the permeability, $\omega$ is the angular frequency, $\sigma$ is the conductivity, and $\delta$ is the skin depth. Equation 5 shows that the phase of the magnetic field at depth z lags the source signal by angle $\delta$. Optimization of the device for detection of defects at this depth requires careful control of the phase of the feedback source 170 so as to maximize the change in amplitude from the defect. The rotating probe assembly 1020 comprises the GMR sensor 130, excitation coil 110 and feedback coil 140, as well as the stepper motor, Hall sensor and push button. The stepper motor and driver, push button and Hall sensor are located on the probe head 1050. The push button and key press detector are used for data display. The Hall sensor and Hall sensor detector are used to detect the probe's 100 position. A D.C. shift of the feedback coil signal would be added when the feedback coil 140 is used for both A.C. feedback and sensor biasing.

Figure 16:
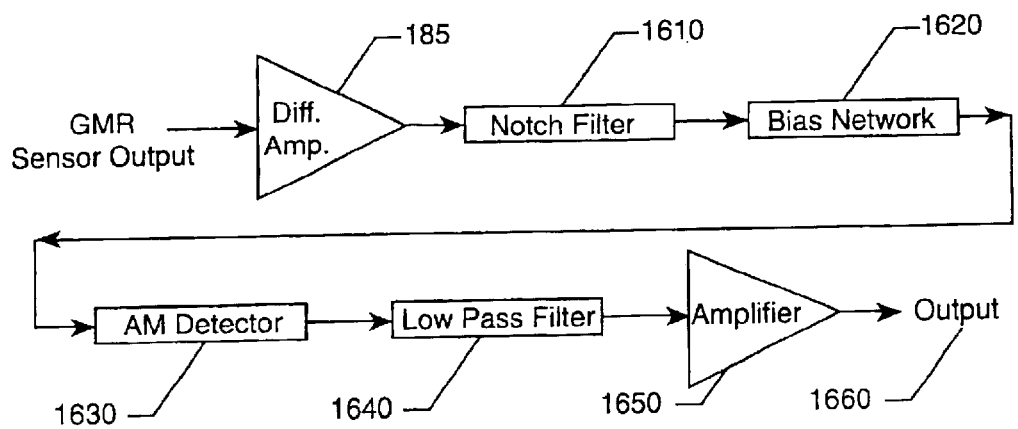
FIG. 16 shows signal detection circuitry.

The signal detector circuitry of FIG. 15 is expanded in the detector embodiment illustrated in FIG. 16. As discussed for an earlier embodiment, a major source of signal interference for the GMR-based device is stepper motor noise. An oscillation in the magnetic field is observed as the twelve pole pairs of the permanent magnet rotor rotate within the stepper motor. The high Q notch filter 1610 in FIG. 16 is therefore centered at 12×(rotation frequency). A probe rotation frequency of 3 Hz was used, such that the notch filter 1610 was centered at 36 Hz. The amplitude modulation detector 1630, requiring biasing 1620, is then used to capture the change in amplitude of the signal due to the probe-to-sample interaction. A low pass filter 1640 is next applied to highlight the effects of fatigue cracks as well as probe alignment position. Finally, this signal is amplified 1650 and sent as output 1660 to an A-D converter to be read by the computer and processed. The FIG. 16 detection circuitry replaces differential amplifier 185 and peak to peak detector 1010.

Figure 17:
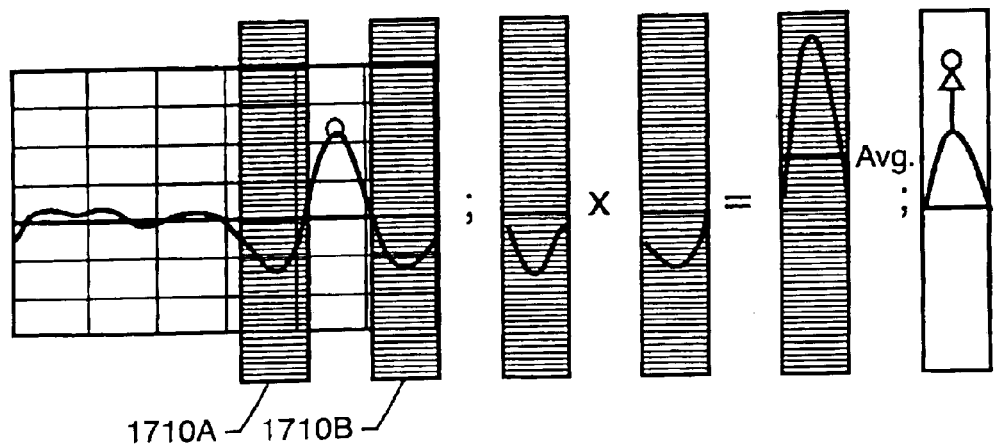
FIG. 17 shows the sliding filter technique for the rotating probe.

A further embodiment, shown in FIG. 17 incorporates a simple "sliding" filtering scheme for improved response of the system. In all cases, the angular position of a flaw correlates with a peak in the output voltage, while two minima are observed on either side lobe of this peak. The position of these side lobe minima relates directly to the spatial frequency of the flaw which is a direct function of the rotation radius and probe footprint. As illustrated schematically in FIG. 17, the processed data amplitude is windowed into two segments 1710A and 1710B with width equal to one half the period of the flaw frequency. The spacing between the two windows is set such that a full period separates the center position of the two arrays. The data in one of the arrays is then reversed and the two are multiplied point by point. The average value of the array product is then calculated and added to the probe response amplitude at the point centered directly between the two windows. The processing is applied equally to each point as the two windows slide in unison through the data.

The incorporation of the additional detection electronics in FIG. 16 provides the control computer 1030 with a deep flaw signal response very similar to that of the near surface response of the probe described in U.S. Pat. No. 5,617,024. The standard filtering techniques developed for that pickup coil-based instrument are thus directly applicable to the present invention. Spatial Fourier filtering can be applied to the amplitude of the sensor output. The use of lower drive frequencies requires only a slight adjustment in the band pass parameters in order to account for the more diffusive lower frequency eddy current distribution.

Experimental results were obtained with a riveted aluminum alloy sample consisting of a stack of 1.0 mm thick aluminum 2024 plates fastened together with threaded rivets to enable inspection of flaws at variable depths.

Figure 18A:
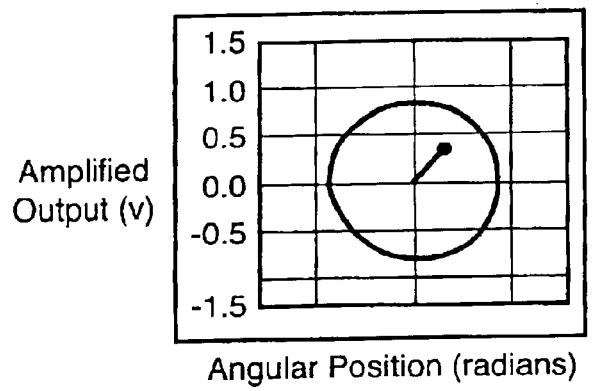
FIG. 18A shows amplified output for a 3.8 mm, 4th layer flaw using the detection electronics of FIG. 16.
Figure 18B:
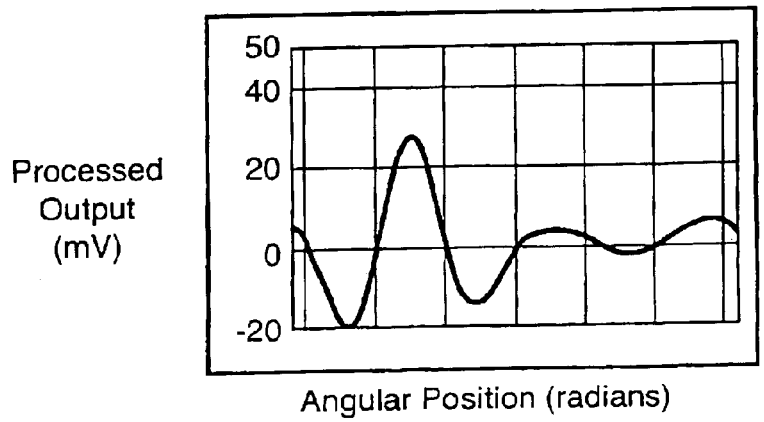
FIG. 18B shows output for a 3.8 mm, 4th layer flaw using spatial Fourier filtering.

FIGS. 18A and 18B display the raw and processed (spatially Fourier filtered) response, output 1660, of the system for a 3.8 mm long $4^{th}$ layer flaw. An operating frequency of 1.3 kHz, rotation radius of 5.5 mm, and spatial bandpass filter between 2.5 and 7.5 cycles per revolution were used in acquiring the data. The polar plot, FIG. 18A, displays the raw amplified probe output amplitude while FIG. 18B shows the processed data as a function of angular position in radians. The characteristic flaw signal in the processed data is clearly evident at an angular position of approximately −1.5 radians.

Figure 19A:
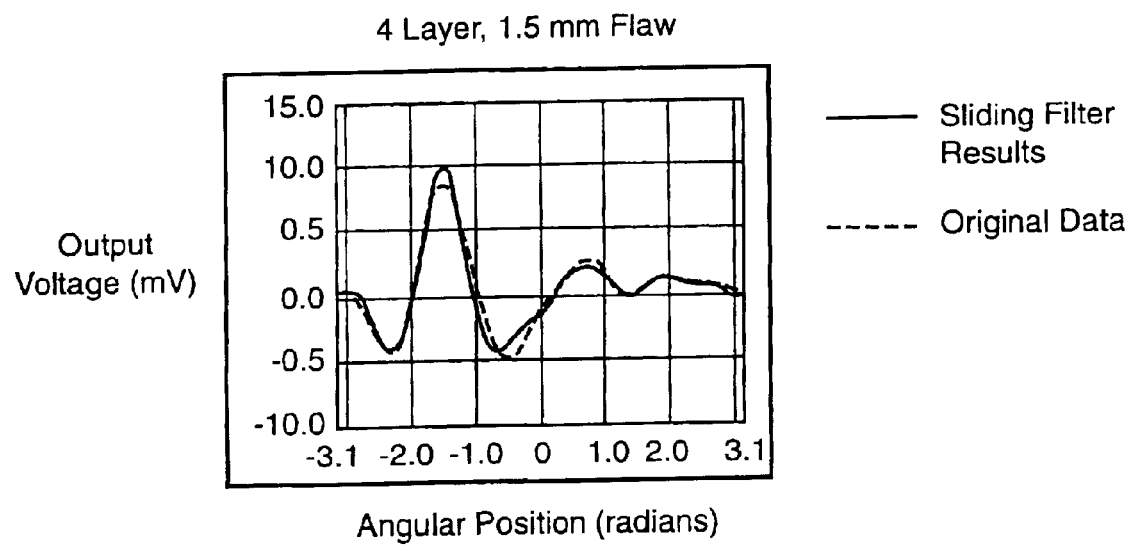
FIG. 19A shows the results of applying the sliding filter to a 1.5 mm, $4^{th}$ layer flaw.
Figure 19B:
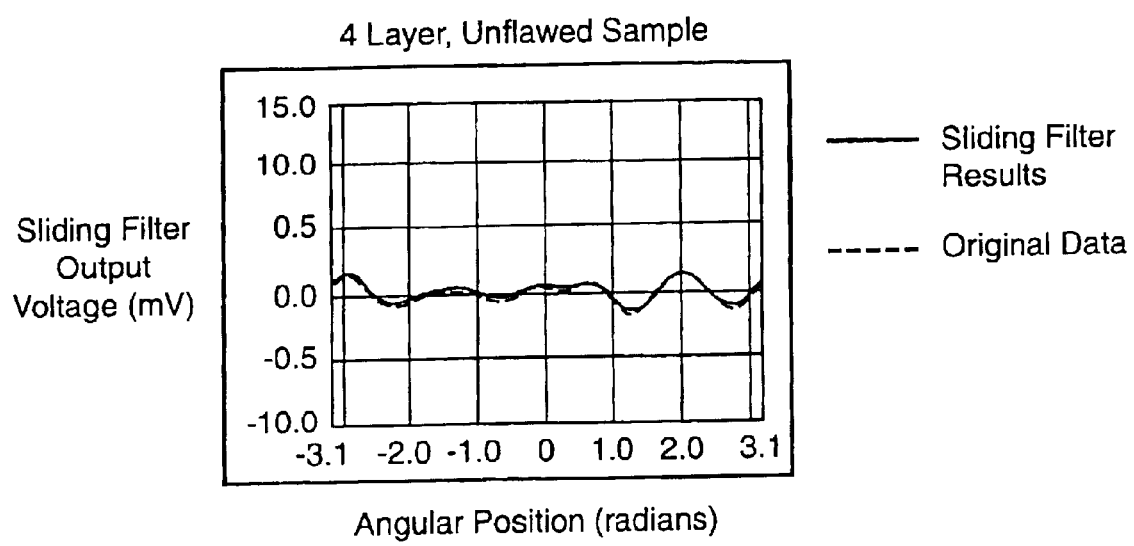
FIG. 19B shows the results of applying the sliding filter to an unflawed rivet joint.

FIGS. 19A and 19B show the results of applying the sliding filter to a 1.5 mm $4^{th}$ layer flaw as well as an unflawed rivet joint. The filter is seen to clearly enhance the system output for the flawed fastener, FIG. 19A. The peak output value increased from 8.4 mV to 10.9 mV. The filtered results show a slightly narrower response to the flaw, with peak position remaining at the angular location of the $4^{th}$ layer EDM notch. Data away from the flaw center show very little effect from the sliding filter as positive and negative fluctuations across the windowed arrays average out. This is also clearly displayed in the data for the unflawed fastener, FIG. 19B. The sliding filter has very little effect as it passes through the data.

Figure 20:
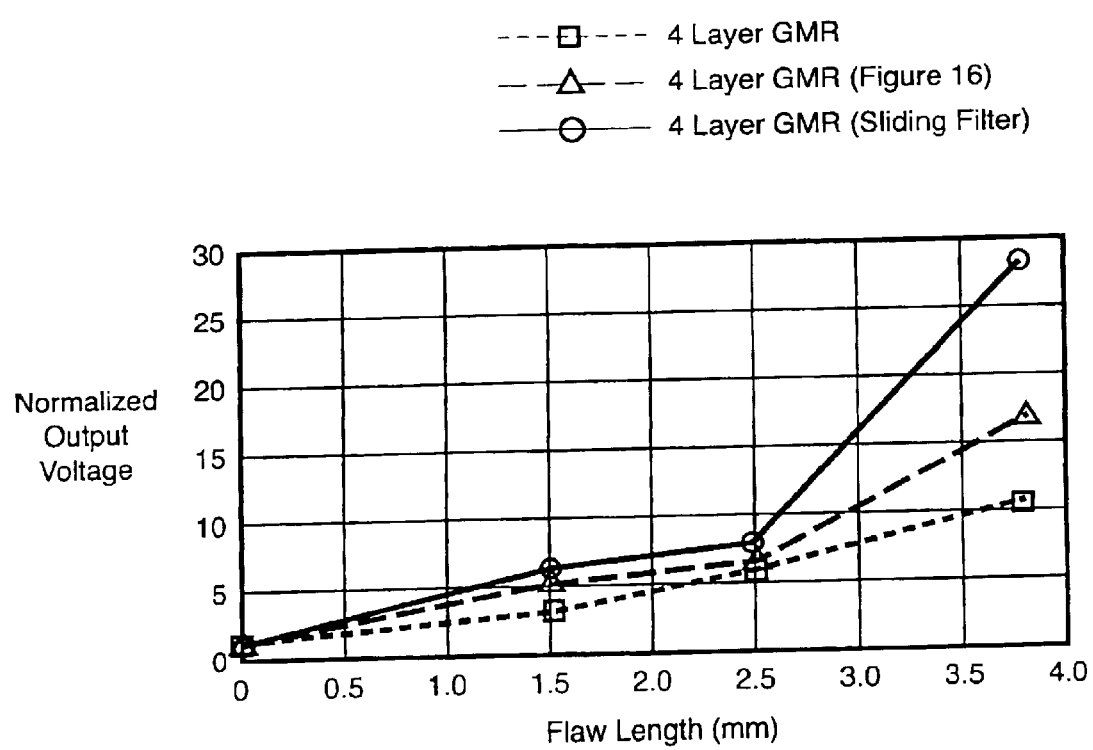
FIG. 20 shows comparison of normalized outputs for 4th layer flaw detection at an airframe fastener.

The performance of the probe for deep flaw detection is summarized in FIG. 20. This graph displays the system output voltages for 1.5, 2.5, and 3.8 mm long EDM notches in the $4^{th}$ layer of the airframe lap-splice joint sample described earlier. The data are normalized to the output recorded for an unflawed fastener.

Although our invention has been illustrated and described with reference to the preferred embodiment thereof, we wish to have it understood that it is in no way limited to the details of such embodiment, but is capable of numerous modifications for many mechanisms, and is capable of numerous modifications within the scope of the appended claims.

What is claimed as new and desired to be secured by Letters Patent of the United States is:

1. An eddy current device for non-destructive evaluation of an electrically conductive material, comprising:
   an excitation coil for inducing eddy currents within the electrically conductive material, the excitation coil having windings wherein the excitation coil's longitudinal axis is perpendicular to the surface of the electrically conductive material;
   a giant magnetoresistive sensor having a longitudinal axis perpendicular to the surface of the electrically conductive material and surrounded by the windings of the excitation coil;
   a tubular flux focusing lens disposed between the excitation coil and the giant magnetoresistive sensor, composed of a conductive material having a high magnetic permeability, having a first opening opposite the surface of the electrically conductive material and having a second opening adjacent to the surface of the electrically conductive material and which prevents magnetic coupling between the excitation coil and the giant magnetoresistive sensor and which produces high flux density at the outer edge of the giant magnetoresistive sensor;
   a feedback source; and
   a feedback coil electrically connected to the feedback source and positioned adjacent to the giant magnetoresistive sensor along the longitudinal axis thereof and surrounded by the windings of the excitation coil and the flux focusing lens, the feedback coil receiving a feedback current from the feedback source having the same frequency as the excitation coil frequency but 180 degrees out of phase with the output of the giant magnetoresistive sensor, such that leakage magnetic fields are canceled.

2. The eddy current device as recited in claim 1, wherein the windings of the excitation and feedback coils are substantially circular.

3. The eddy current device as recited in claim 2, wherein the excitation coil is substantially concentrically disposed around the giant magnetoresistive sensor and the feedback coil.

4. The eddy current device is recited in claim 3, wherein the flux focusing lens is substantially cylindrical and the excitation coil is concentrically disposed around the flux focusing lens.

5. An eddy current device as recited in claim 1, additionally comprising means for applying a drive current to the windings of the excitation coil, wherein the frequency is dependent on the desired depth of flaw detection.

6. An eddy current device as recited in claim 5, wherein the thickness of the flux focusing lens is at least three skin depths of a magnetic flux generated by the drive current applied to the excitation coil.

7. An eddy current device as recited in claim 1, additionally comprising biasing means for biasing the giant magnetoresistive sensor in its linear region.

8. The eddy current device as recited in claim 7, wherein the biasing means is a D.C. voltage applied to the feedback coil.

9. The eddy current device as recited in claim 7, wherein the biasing means is a permanent magnet positioned adjacent to the giant magnetoresistive sensor.

10. The eddy current device as recited in claim 1, further comprising:
    an amplifying means for amplifying the output of the giant magnetoresistive sensor; and
    a detection means for registering the output of the amplifying means.

11. The eddy current device as recited in claim 10, wherein the amplifying means is a differential preamplifier.

12. The eddy current device as recited in claim 10, wherein the detection means is an A.C. voltmeter.

13. The eddy current device as recited in claim 1, wherein the giant magnetoresistive sensor is a packaged eight pin integrated chip.

14. The eddy current device as recited in claim 1, wherein the giant magnetoresistive sensor is in its die form.

15. The eddy current device as recited in claim 1, wherein the height of the giant magnetoresistive sensor is less than the half height of the flux focusing lens.

16. The eddy current device as recited in claim 1, wherein the height of the giant magnetoresistive sensor is less than one half the height of the excitation coil.

17. The eddy current device as recited in claim 1, wherein the bottom edge of the giant magnetoresistive sensor is co-planar with the bottom edge of the excitation coil and the second opening of the flux focusing lens.

18. The eddy current device as recited in claim 1, further comprising processing means for processing the giant magnetoresistive sensor output.

19. The eddy current device as recited in claim 18, wherein the processing means comprises data analysis obtaining a phase rotated amplitude, flattening the phase rotated amplitude and applying a low pass two-dimensional Fourier filter.

20. An eddy current device resistant to conductive material edge effects for non-destructive evaluation of an electrically conductive material comprising:
    an excitation coil for inducing eddy currents within the electrically conductive material, the excitation coil having windings wherein the excitation coil's longitudinal axis is perpendicular to the surface of the electrically conductive material;
    a giant magnetoresistive sensor having a longitudinal axis perpendicular to the surface of the electrically conductive sample and surrounded by the windings of the excitation coil;
    a tubular flux focusing lens disposed between the excitation coil and the giant magnetoresistive sensor, composed of a conductive material having a high magnetic permeability, having a first opening opposite the surface of the electrically conductive material and having a second opening adjacent to the surface of the electrically conductive material and which prevents magnetic coupling between the excitation coil and the giant magnetoresistive sensor and which produces high flux density at the outer edge of the giant magnetoresistive sensor;
    a feedback source;

a feedback coil electrically connected to the feedback source and positioned adjacent to the giant magnetoresistive sensor along the longitudinal axis thereof and surrounded by the windings of the excitation coil and the flux focusing lens, the feedback coil receiving a feedback current from the feedback source having the same frequency as the excitation coil frequency but 180 degrees out of phase with the output of the giant magnetoresistive sensor, such that leakage magnetic fields are canceled; and a flux focusing shield which surrounds the excitation coil.

21. An eddy current device resistant to conductive material edge effects as recited in claim 20, wherein the flux focusing shield is composed of a conducting material of high magnetic permeability.

22. A magnetoresistive flux focusing eddy current device for non-destructive evaluation of an electrically conductive material surrounding a circular inhomogeneity, comprising:

an excitation coil for inducing eddy currents within the electrically conductive material, the excitation coil having windings wherein the excitation coil's longitudinal axis is perpendicular to the surface of the electrically conductive material;

a giant magnetoresistive sensor having a longitudinal axis perpendicular to the surface of the electrically conductive sample and surrounded by the windings of the excitation coil;

a tubular flux focusing lens disposed between the excitation coil and the giant magnetoresistive sensor, composed of a conducting material having a high magnetic permeability, having a first opening opposite the surface of the electrically conductive material and having a second opening adjacent to the surface of the electrically conductive material and which prevents magnetic coupling between the excitation coil and the giant magnetoresistive sensor and which produces high flux density at the outer edge of the giant magnetoresistive sensor;

a feedback source;

a feedback coil electrically connected to the feedback source and positioned adjacent to the giant magnetoresistive sensor along the longitudinal axis thereof and surrounded by the windings of the excitation coil and the flux focusing lens, the feedback cool receiving a feedback current from the feedback source having the same frequency as the excitation coil frequency but 180 degrees out of phase with the output of the giant magnetoresistive sensor, such that leakage magnetic fields are canceled; and rotator means for rotating the device about the circular inhomogeneity such that the center of the device remains a constant distance from the center of the circular inhomogeneity.

23. The eddy current device of claim 22, further comprising:

an amplifying means for amplifying the output of the giant magnetoresistive sensor;

a detection means for registering the output of the amplifying means;

monitoring means for monitoring the output of the giant magnetoresistive sensor; and scanning means for scanning the device about the circumference of the circular inhomogeneity.

24. The eddy current device as recited in claim 23, wherein the amplifying means is a differential amplifier.

25. The eddy current device as recited in claim 23, wherein the detection means is a peak to peak detector.

26. The eddy current device as recited in claim 23, wherein the monitoring means is a computer.

27. The eddy current device as recited in claim 23, wherein the scanning means is a stepper motor.

28. The eddy current device as recited in claim 23, wherein the detection means comprises amplified low pass filtering of an amplitude modulated notch-filtered giant magnetoresistive sensor signal.

29. An eddy current device as recited in claim 28, further comprising spatial Fourier filtering of the amplified low-pass filtered signal.

30. An eddy current device as recited in claim 29, further comprising:

windowing the filtered data amplitude into two segment arrays, each segment array having a width equal to one half the period of the flaw frequency, wherein the spacing between the two windows is set such that a full period separates the center position of the two segment arrays;

reversing the data in one of the arrays;

multiplying the reversed and nonreversed arrays;

calculating the average value of the array product; and adding the average value to the device response amplitude at the point centered directly between the two windows.

31. An eddy current device as recited in claim 22, additionally comprising means for applying a drive current to the windings of the excitation coil, wherein the frequency is dependent on the desired depth of flaw detection.

32. An eddy current device as recited in claim 31, further comprising computer control of the amplitude, frequency, and phase angle of the source signals to the feedback and excitation coils.

* * * * *